US005653749A

United States Patent [19]
Love et al.

[11] Patent Number: 5,653,749
[45] Date of Patent: Aug. 5, 1997

[54] PREFABRICATED, STERILE AND DISPOSABLE KITS FOR THE RAPID ASSEMBLY OF A TISSUE HEART VALVE

[75] Inventors: Charles S. Love, Camarillo; John H. Calvin, Carpenteria, both of Calif.

[73] Assignee: Autogenics, Glasgow, United Kingdom

[21] Appl. No.: 252,690

[22] Filed: Jun. 2, 1994

Related U.S. Application Data

[60] Continuation of Ser. No. 925,376, Aug. 3, 1992, Pat. No. 5,326,370, which is a division of Ser. No. 646,001, Jan. 24, 1991, Pat. No. 5,163,955.

[51] Int. Cl.$^6$ ........................................................ A61F 2/24
[52] U.S. Cl. ........................................................ 623/2
[58] Field of Search ................................ 623/2, 66, 900, 623/901

[56] References Cited

U.S. PATENT DOCUMENTS

| | | |
|---|---|---|
| 2,822,819 | 2/1958 | Geeraert . |
| 2,922,437 | 1/1960 | Rippingille . |
| 3,026,823 | 3/1962 | Wilcox . |
| 3,532,016 | 10/1970 | Lane . |
| 3,548,418 | 12/1970 | Angell et al. . |
| 3,570,014 | 3/1971 | Hancock . |
| 3,574,865 | 4/1971 | Hamaker . |
| 3,589,392 | 6/1971 | Meyer . |
| 3,714,671 | 2/1973 | Edwards et al. . |
| 3,755,823 | 9/1973 | Hancock . |
| 3,967,645 | 7/1976 | Gregory . |
| 3,983,581 | 10/1976 | Angell et al. . |
| 4,011,947 | 3/1977 | Sawyer . |
| 4,035,849 | 7/1977 | Angell et al. . |
| 4,065,816 | 1/1978 | Sawyer . |
| 4,084,268 | 4/1978 | Ionescu et al. . |
| 4,101,031 | 7/1978 | Cromie . |
| 4,106,129 | 8/1978 | Carpentier et al. . |
| 4,172,295 | 10/1979 | Batten . |
| 4,182,446 | 1/1980 | Penny . |
| 4,192,020 | 3/1980 | Davis et al. . |
| 4,211,241 | 7/1980 | Kaster et al. . |
| 4,247,292 | 1/1981 | Angell . |
| 4,297,749 | 11/1981 | Davis et al. . |
| 4,388,735 | 6/1983 | Ionescu et al. . |
| 4,470,157 | 9/1984 | Love . |

(List continued on next page.)

FOREIGN PATENT DOCUMENTS

| | | |
|---|---|---|
| 1243453 | 10/1988 | Canada . |
| 0051451 | 5/1982 | European Pat. Off. . |
| 0116236 | 8/1984 | European Pat. Off. . |
| 0179562 | 4/1986 | European Pat. Off. . |
| 2391708 | 12/1978 | France . |
| 2399832 | 4/1979 | France ........................................ 623/2 |
| 1189399 | 4/1970 | United Kingdom . |
| 1264472 | 2/1972 | United Kingdom . |
| 1598112 | 2/1978 | United Kingdom . |
| 2046165 | 11/1980 | United Kingdom . |
| 2169386 | 1/1986 | United Kingdom . |
| 9115167 | 10/1991 | WIPO . |

OTHER PUBLICATIONS

The Autogenous Tissue Heart Valve: Current Status: Charles S. Love, B.A., and Jack W. Love, D. Phil., M.D.: vol. 6, No. 4, 1991.

Barratt–Boyes, "A Method for Preparing and Inserting a Homograft Aortic Valve", Brt. J. Surg. Nov. 1965, vol. 52, No. II, pp. 847–856.

(List continued on next page.)

*Primary Examiner*—David H. Willse
*Attorney, Agent, or Firm*—Knobbe, Martens, Olson & Bear, LLP

[57] ABSTRACT

This invention relates generally to a rapid assembly, concentric and flexible mating stent, tissue heart valve which can be assembled from prefabricated, sterile kits by a non-surgeon in the limited time available in an operating room. The kits provide the necessary tools and apparatus for harvesting the tissue and measuring the open annulus within the patient's heart. In addition, the kits contain size-specific components to be used during the rapid manufacture of the tissue heart valve.

4 Claims, 25 Drawing Sheets

U.S. PATENT DOCUMENTS

| | | |
|---|---|---|
| 4,490,859 | 1/1985 | Black et al. . |
| 4,501,030 | 2/1985 | Lane . |
| 4,512,471 | 4/1985 | Kaster et al. . |
| 4,523,592 | 6/1985 | Daniel . |
| 4,535,819 | 8/1985 | Atkinson et al. . |
| 4,597,767 | 7/1986 | Lenkei . |
| 4,605,407 | 8/1986 | Black et al. . |
| 4,643,732 | 2/1987 | Pietsch et al. . |
| 4,679,556 | 7/1987 | Lubock et al. . |
| 4,687,483 | 8/1987 | Fisher et al. . |
| 4,692,164 | 9/1987 | Dzemeshkevich et al. . |
| 4,725,274 | 2/1988 | Lane et al. . |
| 4,801,015 | 1/1989 | Lubock et al. . |
| 4,838,288 | 6/1989 | Wright et al. . |
| 4,881,562 | 11/1989 | Wright et al. . |
| 4,955,325 | 9/1990 | Zarnowski et al. ............... 623/22 |
| 5,037,434 | 8/1991 | Lane . |
| 5,147,391 | 9/1992 | Lane . |
| 5,163,955 | 11/1992 | Love et al. . |
| 5,326,370 | 7/1994 | Love et al. ....................... 623/2 |
| 5,326,371 | 7/1994 | Love et al. . |
| 5,423,887 | 6/1995 | Love et al. . |
| 5,425,741 | 6/1995 | Lemp et al. ..................... 606/167 |

OTHER PUBLICATIONS

Reis, et al., "The flexible stent: A new concept in the fabrication of tissue heart valve prostheses", The Journal of Thoracic and Cardiovascular Surgery, Nov. 1971, vol. 62, No. 5, pp. 693–689; 693–695.

Yates, "A fascial frustum valve for aortic valve–repalcement", Thorax, 1971, vol. 26, pp. 184–189.

Brownlee, et al., "A fascia lata mitral valve based on the 'frustum' principle", Thorax, 1971, vol. 26, pp. 284–287.

Bartek, et al., "Frame–mounted tissue heart valves: technique of construction", Thoraz, 1974, vol. 29, pp. 51–55.

Ionescu, et al., "Replacement of heart valves with frame–mounted tissue grafts", Thorax, 1974, vol. 29, pp. 56–67.

Black, et al., "A construction technique for minimizing valve leaflet fatigue failure in pericardial valves", Life Support Systems, Proceedings XI Annual Meeting ESAO, Alpbach–Innabruck, Austria, Sep. 1984, vol. 2, Supp. 1.

Love, "An Alternate Method for Applying a Dacron Cover to a Delrin Bioprosthetic heart Valve Stent", Proceedings of the Third Southern Biomedical Engineering Conference, Pergamon Press, 1984, pp. 30–37.

Love, et al., "Rapid Intraoperative Fabrication of an Autogenous Tissue heart Valve: A New Technique", Proceedings of the Third International Symposium of Cardiac Biprosthesis, Yorke Medical Books, New York, N.Y., 1986, pp. 691–698.

Love, et al., "Degenerative calcification in tissue valves a metabolic/hemodynamic or immunologic problem?", Abstract published for the International Associate for Cardiac Biological Implants, Chicago, Apr. 5, 1987, p. 1.

Love, et al., "Experimental Evaluation of an Autogenous Tissue Heart Valve", Poster Presentation at the Fifth International Symposium Cardiac Bioprostheses, San Diego, Apr. 15, 1988.

Ruel, et al., "In Vitro Testing of Bioprostheses", Trans. Am. Soc. Artif. Intern. Organs, 1988, vol. XXXIV, pp. 1033–1039.

Love, et al., "The Autogenous Tissue Heart Valve: Experience with Pericardium", Pericardial Tissue as a Cardiac Valve Substitute, Proceedings of a Symposium, Thumberbach, Austria, Sep. 1988, pp. 31–40.

Matsuda, et al., "A Hand–Made Valved Conduit with High–Porosity Knitted Graft and Glutaraldehyde–Treated Autologous Pericardial Trileaflet Valve", Abstracts of the VII World Congress Artificial Organs, 1989, vol. 13, No. 4.

Khan, et al., "Doppler and Hemodynamic Characteristics of the Autogenics Bioprosthetic Valve":, p. 1.

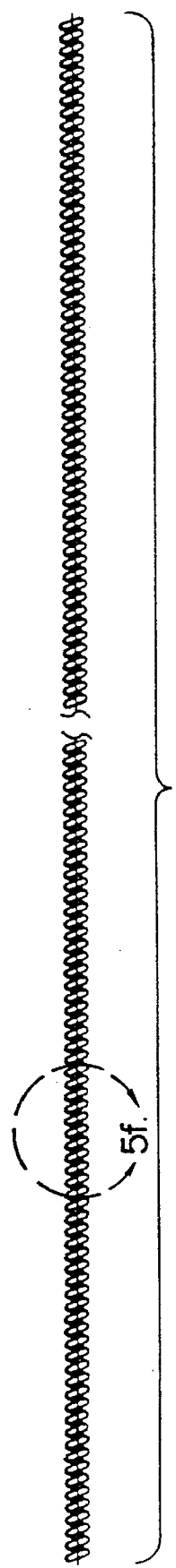
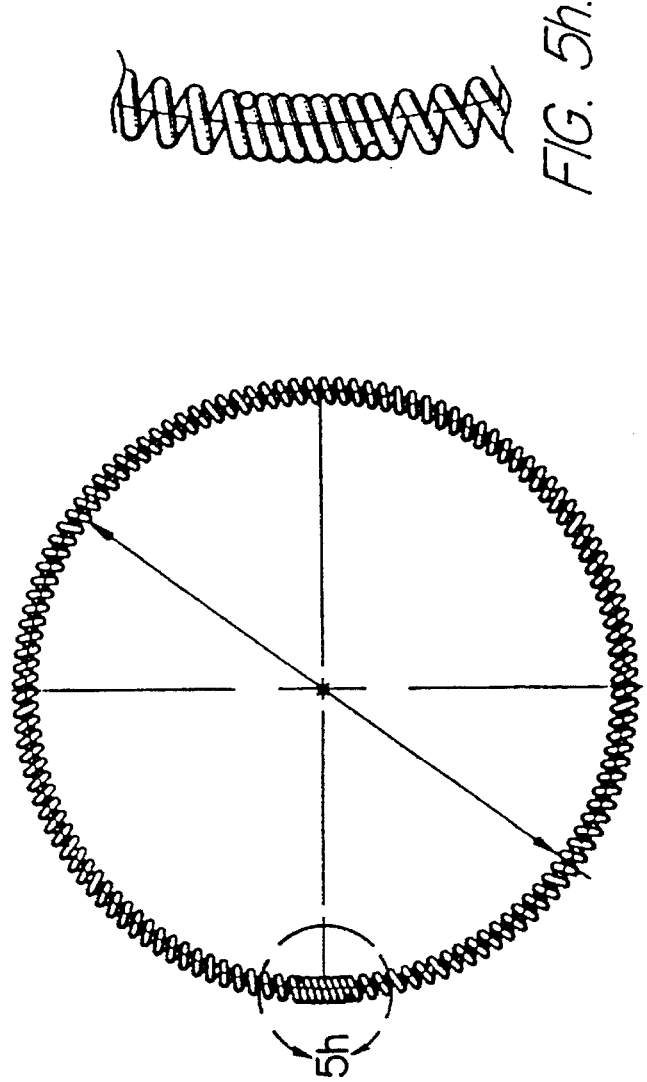
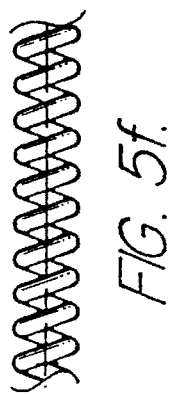
FIG. 5e.
FIG. 5f.
FIG. 5g.
FIG. 5h.

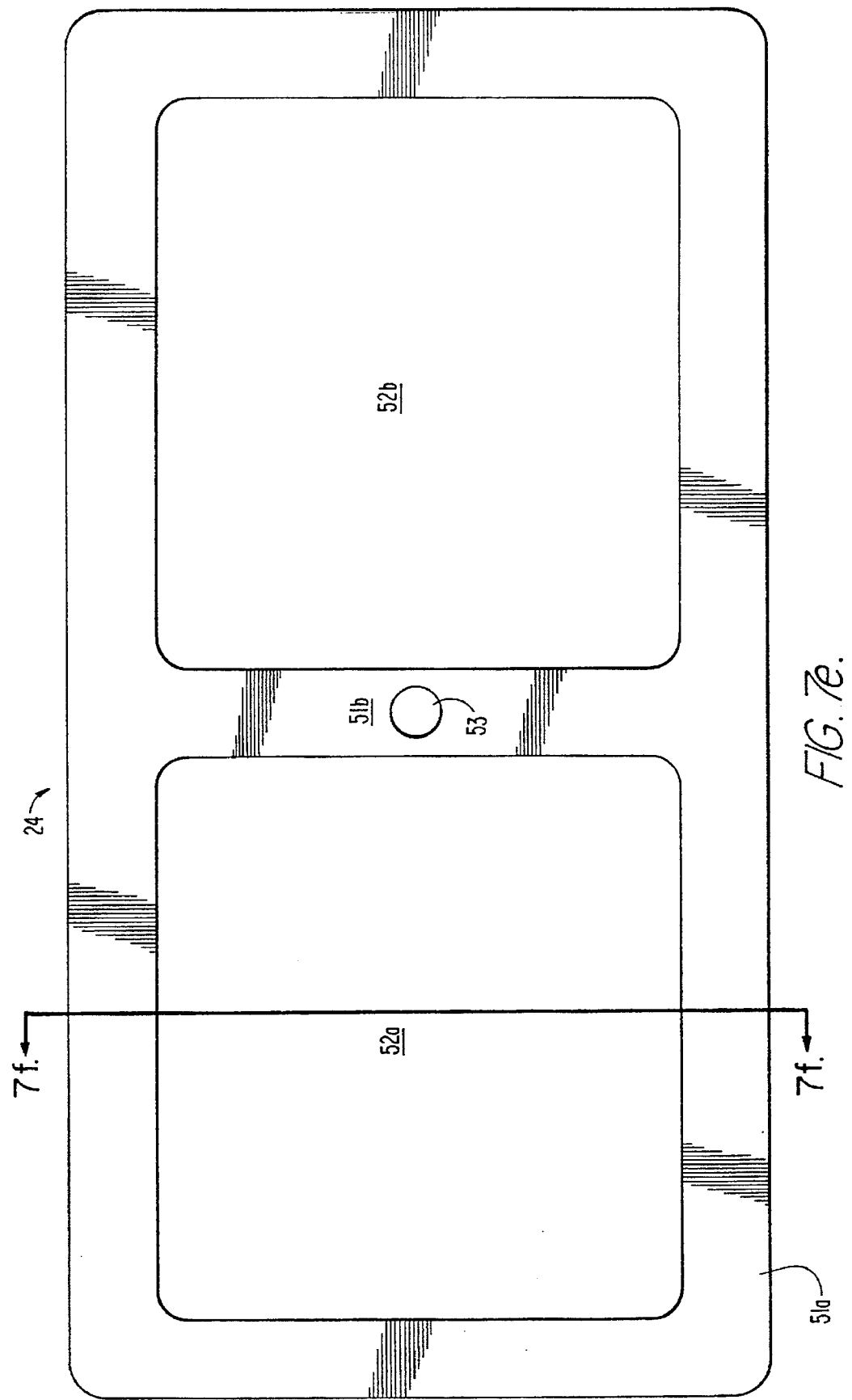

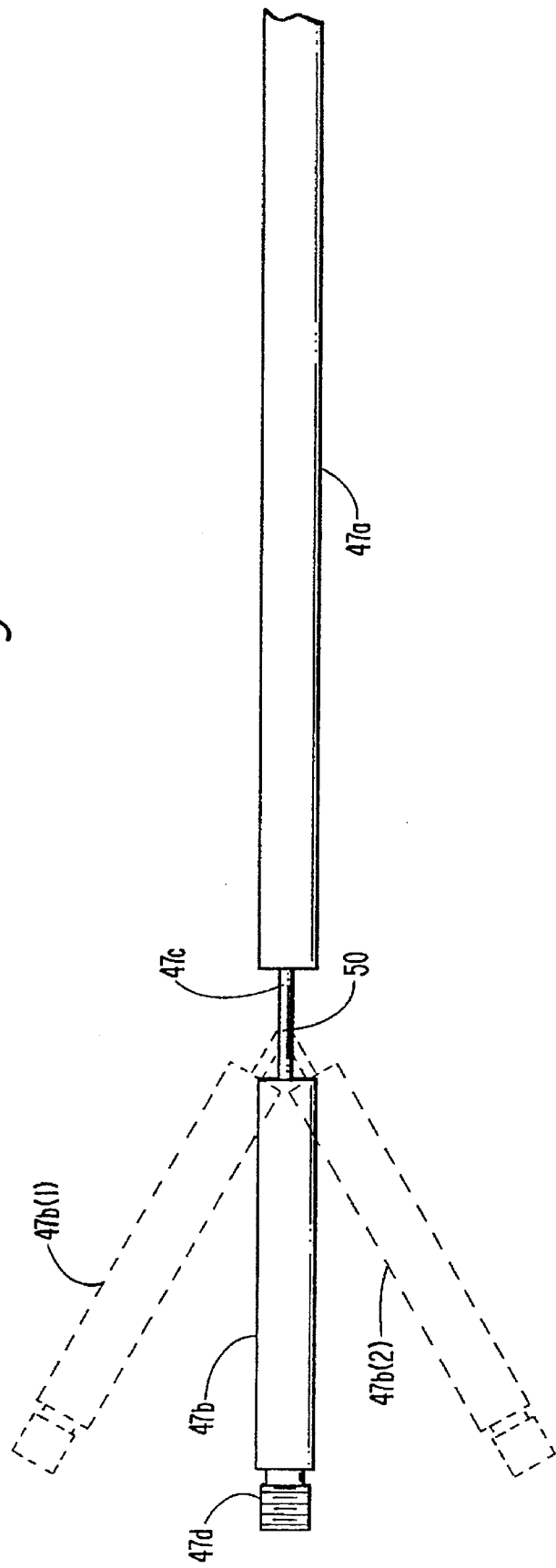

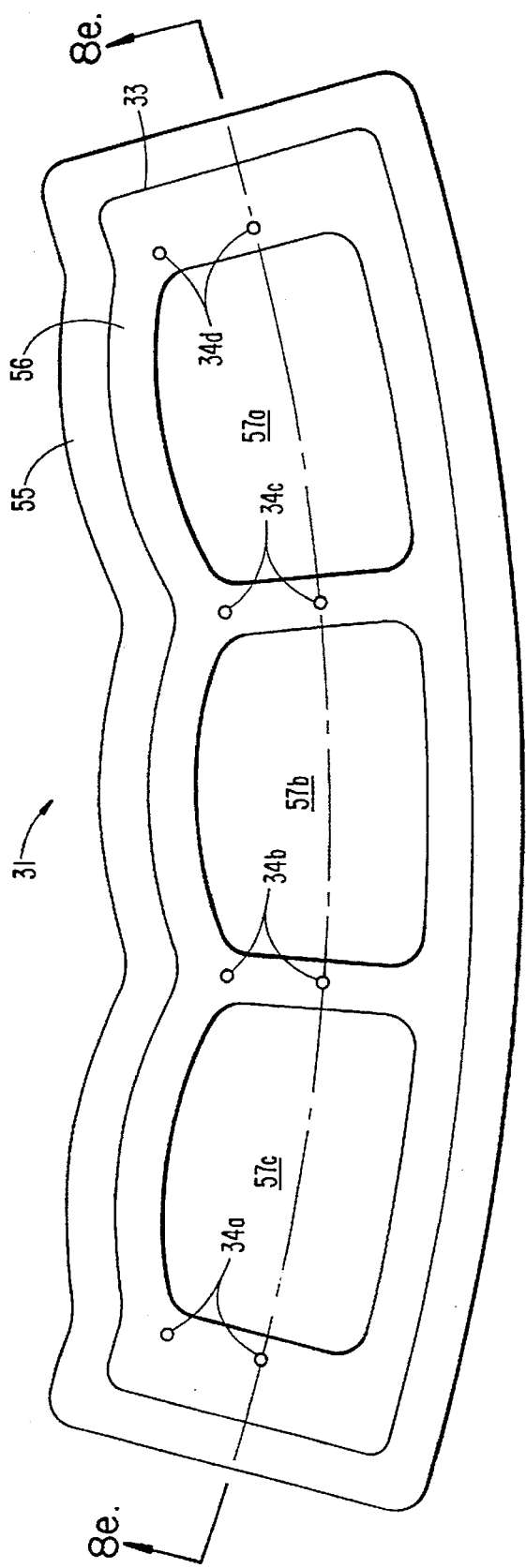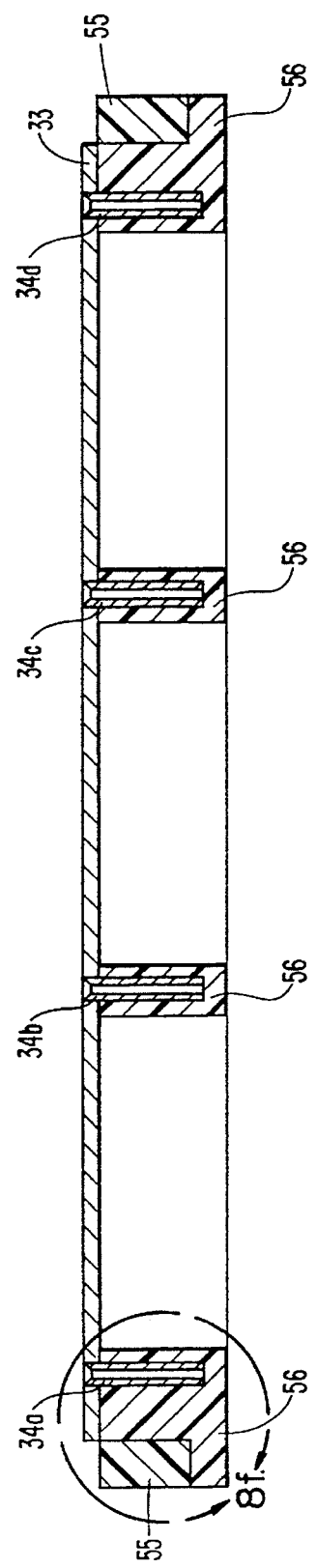

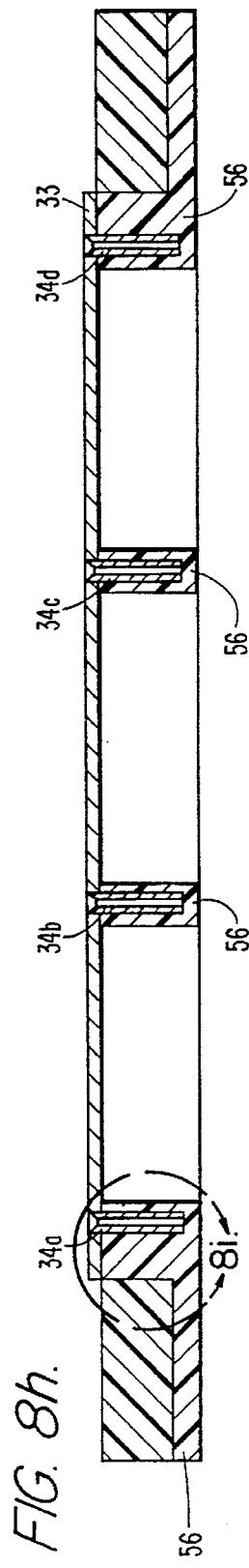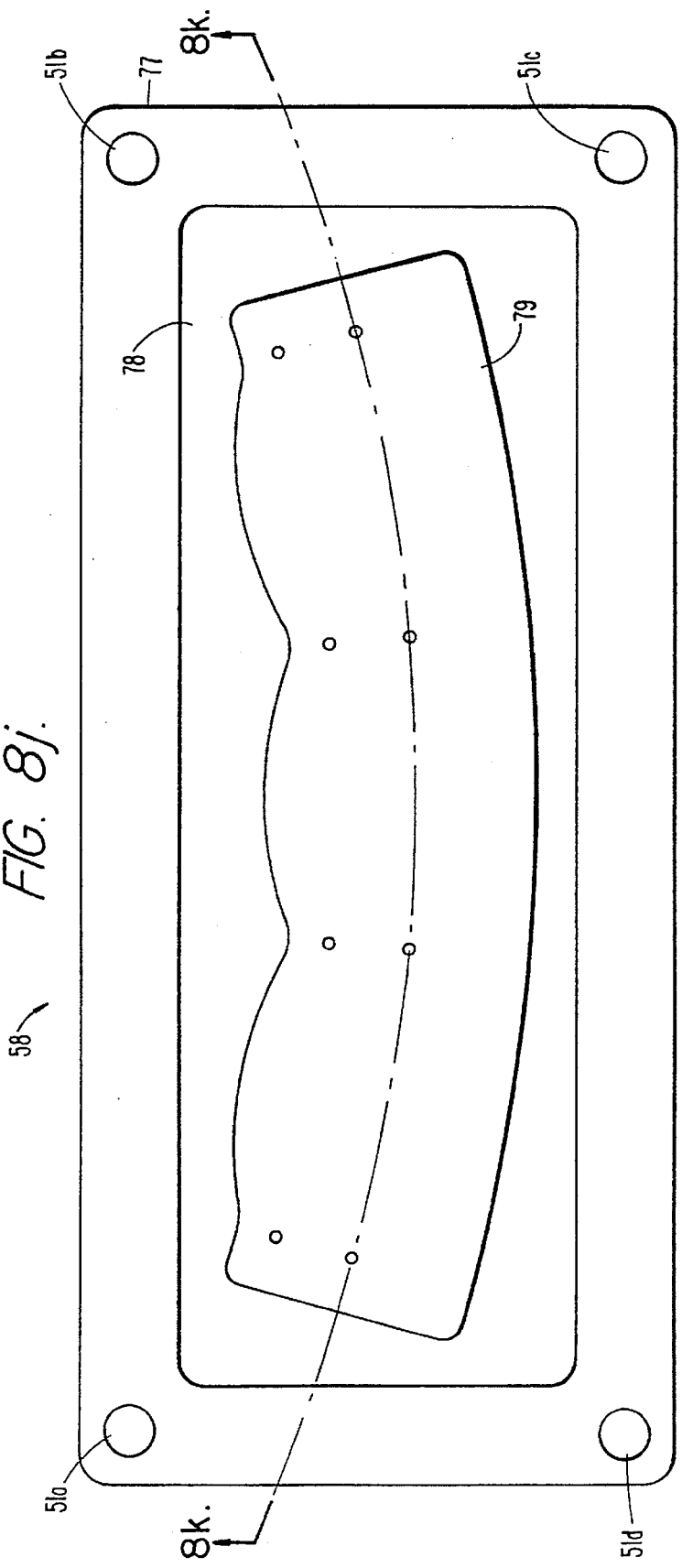

PREFABRICATED, STERILE AND DISPOSABLE KITS FOR THE RAPID ASSEMBLY OF A TISSUE HEART VALVE

This application is a continuation of U.S. application Ser. No. 07/925,376, filed Aug. 3, 1992, now U.S. Pat. No. 5,326,370, which is a divisional application of U.S. application Ser. No. 07/646,001, filed Jan. 24, 1991, now U.S. Pat. No. 5,163,955.

BACKGROUND OF THE INVENTION

I. Field of the Invention

This invention relates generally to a rapid assembly, concentric and flexible mating stent, tissue heart valve which substantially substitutes clamping of the tissue for sewing, and more specifically, to such a valve which can be assembled from prefabricated kits by a non-surgeon in the limited time available in an operating room, which is configured to substantially uniformly clamp the tissue between the stents and securely hold the tissue in place after valve assembly, which is also configured with tissue alignment members to provide enhanced alignment of the tissue between the stents during valve assembly. After valve assembly, the tissue is held in place by the clamping force of the stents.

II. Background of the Invention

Several types of heart valves are presently available for use in replacing diseased or malfunctioning heart valves in humans.

One such valve is an animal tissue valve, constructed utilizing bovine tissue or porcine aortic valve tissue or the like. These valves typically must be constructed by a trained specialist in a laboratory setting well in advance of when they will be needed to replace a diseased or malfunctioning human heart valve, and then stored in an aldehyde solution until they are needed.

Although these valves have proven to have acceptable hemodynamics, they typically suffer from a durability problem, which requires that these valves be replaced after about five to ten years of use. This is a significant problem because, after a first implant of a heart valve, subsequent implants in the same area of the heart are more difficult and risky to the patient.

The durability problem in animal tissue valves arises from two sources. First, the tissue is typically treated with glutaraldehyde or the like to attenuate the antigenicity of the tissue, and this will tan the tissue to a leather-like consistency. As a result, the tissue will become more inflexible, and over time, the valve may wear out from the stress exerted on the valve by the repeated opening and closing of the valve. Second, the antigenicity of the tissue may generate an immunological response which causes the valve to calcify, rendering it inflexible and susceptible to stress. A treatment with glutaraldehyde significantly reduces, but does not completely eliminate, the host body's immunological response to the foreign tissue. Animal tissue valves are typically not recommended for children and young adults precisely because they are not durable enough for them. One theory is that the more active immunological response in children leads to more rapid calcification of these valves, which in turn, causes their reduced durability in children.

Another problem with animal tissue valves is that they require a trained specialist to sew and assemble, and also cannot typically be sewed and assembled in the operating room because of the excessive time required. As a result, they must typically be sewed and assembled in a laboratory setting well before they are needed to replace a diseased or damaged human heart valve. Special facilities are therefore required to process and store the tissue before valve assembly, and to store the assembled valves until they are needed in the operating room. All these factors increase the cost of these valves to the patient.

Another type of valve which is presently available is the mechanical valve. This valve is typically constructed from nonbiological materials such as hard and durable ceramics, metals, and plastics and the like, and therefore, does not suffer from the durability problem associated with animal tissue valves. Because of the nonbiological nature of these valves, however, blood clots and the like can easily form on these valves, with the attendant risk to the patient that the clot fragments could break loose into the arteries, causing an embolism or stroke. This characteristic of mechanical valves is known as thromboembolism. As a result, a patient into which a mechanical valve has been implanted is required to take anticoagulants.

Anticoagulants, however, introduce another set of problems. First, it may be inconvenient for a patient to take anticoagulants. Second, any anticoagulant can lead to hemorrhagic complications in some patients, particularly older patients, with the result that mechanical valves may not be recommended for these patients. Third, some patients may be unreliable about taking their medication, especially in remote areas.

Mechanical valves are also sometimes constructed from expensive material in short supply such as pyrolytic carbon. This factor also increases the cost of these valves to the patient.

As a result, both animal tissue and mechanical valves have not proven to be entirely satisfactory, and other valve types have been explored.

Homograft tissue valves have also become available. These valves have not proven to be entirely satisfactory. Specific limitations of these valves include lack of general availability, antigenicity of the tissue, durability being no better than for animal valves, the requirement of additional surgical training to implant, the requirement of special facilities to harvest and store, the lack of availability in an adequate range of sizes, and the lack of improved performance over xenografts. Homograft valves, as currently used, also have the potential for transmitting viral diseases. All these factors result in increased cost and risk to the patient.

Autogenous tissue valves, i.e., tissue valves constructed with the patient's own tissue, have also been explored. Autogenous tissue valves, however, unlike prior art valves, must, as a practical matter, be capable of being assembled during the same surgical procedure in which the patient's diseased or damaged valve is replaced. This is because these valves cannot practically be assembled in previous surgical procedures since they cannot be sized until the annulus of the patient, into which a replacement valve is to be implanted, has been exposed in the replacement surgical procedure. Although attempts have been made to size the annulus using X-rays or the like, these methods are only approximate and have not proved reliable.

Assembly during the same surgical procedure, however, requires that the autogenous tissues used in these valves be extracted, and then the valves themselves be sized and assembled rapidly to avoid any prolongation of the time that the patient is maintained on a cardio-pulmonary bypass. Typically, 10–15 minutes are required to place anchoring sutures in the valve annulus, and construction of the autogenous tissue valve should be accomplished in that period of time. The autogenous tissue is available for preparation early in the surgical procedure for preliminary preparation.

Attempts have been made to construct autogenous tissue valves in the limited time available while the patient is on the operating table. These attempts, however, were abandoned because of the difficulty encountered in constructing a durable and structurally sound valve in the limited time available, lack of a standardized repeatable method of valve assembly, and poor results with fresh, untreated tissue.

These attempts were abandoned, in part, since the valves were constructed and held together typically by the time-consuming and error-prone method of suturing the tissue to a unitary frame or stent. Not only did this procedure require too much time, i.e., more than 10 minutes, to assemble the valve, but it was also found that the risk of uncertain valve quality, caused by the rushed conditions under which the valves were assembled, was too high. In fact, poor valve quality caused one early researcher to state: "The construction of the graft in the operating theatre during surgery, with a limited amount of time available, does not offer the best conditions for the preparation of a perfect valve." See "Replacement of Heart Valves With Frame-Mounted Tissue Grafts," Ionescu et al., Thorax (1974), Vol. 29, p. 56, at p. 65. This procedure was also expensive and of limited availability, since it typically could only be performed by skilled surgeons. For all the foregoing reasons, these attempts at constructing autogenous tissue valves were abandoned.

In U.S. Pat. No. 4,470,157 (the '157 patent), Jack W. Love, one of the inventors herein, pioneered an autogenous valve which utilized mating stents to clamp the tissue between the stents. This patent did not specifically address the problem of prolapse. This problem occurs when the tissue is not uniformly distributed amongst the leaflets of the valve, the leaflets are not of uniform size, and the co-aptive edges of the leaflets do not meet uniformly during valve closure, resulting in valve leakage and undue stress on the leaflets.

Prolapse can be a significant problem, and later attempts to reduce or eliminate prolapse, such as alignment stitches or the like, have not proven successful in completely eliminating prolapse. This is because the stitches are difficult to accurately place in an operating room environment where time constraints are important.

Another problem not specifically addressed by the '157 patent was the tendency for the tissue between the stents to slip, due to irregularities in the specific tissue used in the valve interfering with the clamping force generated by the stents, and due to the lack of uniformly distributed clamping force both along the annular bases of the stents, and between the stent posts.

U.S. Pat. No. 4,687,483 describes a valve which is assembled by registering a significant number of pins and studs extending from an inner frame to corresponding holes and slots in an outer frame, securing the pins with securing washers, and sewing tissue or cloth frame coverings together. Because of the large number of pins and studs involved, and the sewing required, this valve is not capable of being assembled in the limited time available in an operating room environment. Consequently, this valve is not satisfactory for rapidly assembling an autogenous tissue valve in the operating room.

U.S. Pat. No. 4,192,020 describes a valve which utilizes an adhesive such as polyurethane dissolved in tetrahydrofuran to secure fabric to wire frames. An adhesive such as this is toxic, and not suitable for affixing tissue, especially viable human tissue, to a valve. Consequently, this valve is not satisfactory either for use in assembling an autogenous tissue valve.

U.S. Pat. No. 4,501,030 describes a complex valve which utilizes a significant number of sutures to assemble the valve. Consequently, this valve cannot be assembled in the limited time available either.

In sum, for all the foregoing reasons, it is an object of the present invention to provide a rapid assembly, flexible and concentric mating stent tissue valve that substantially substitutes clamping for sewing, which is configured to generate a substantially uniform clamping force on the tissue between the stents in the assembled valve, and which is configured to generate a self-adjusting clamping force which adjusts for tissue irregularities. It is a further object to provide a valve which achieves proper alignment and prevents movement of the tissue during valve assembly to prevent prolapse. It is a further object to provide a method for assembling such a valve which is standardized and reproducible, and which can easily be learned and practiced by a non-surgeon.

Additional objects and advantages will be set forth in the description which follows or will be apparent to those or ordinary skill in the art who practice the invention.

BRIEF DESCRIPTION OF THE DRAWINGS

FIGS. 5e–5h illustrate, in detail, the garter spring integrated into the outer stent;

FIGS. 7a–7g illustrate the components of the tissue harvesting and annulus sizing kit;

FIGS. 8a–8k illustrate the components of the size-specific stent and valve assembly kit;

SUMMARY OF THE INVENTION

Figure 1:
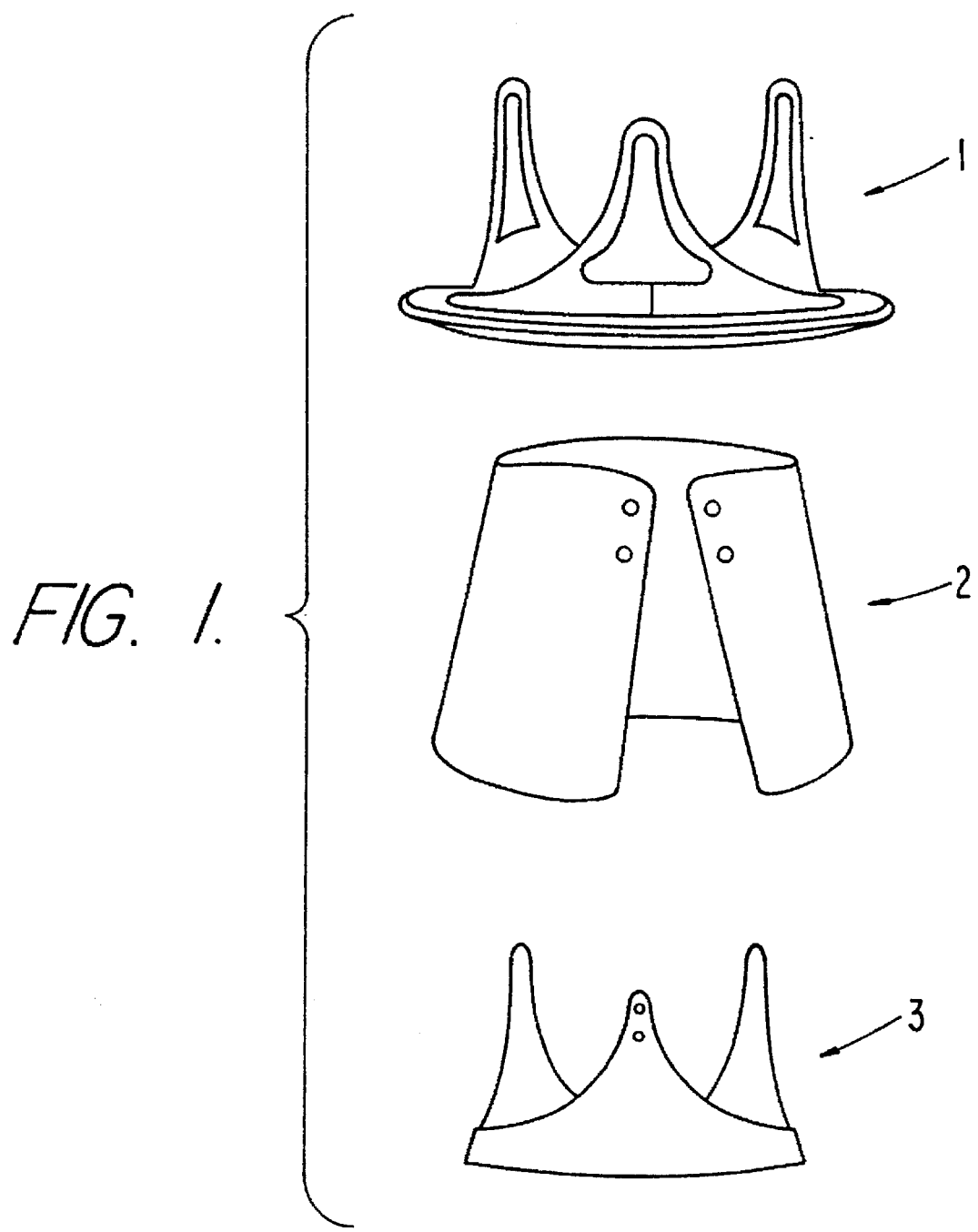
FIG. 1 illustrates the major components in the valve assembly.

In accordance with the purpose of the invention as broadly described herein, there is provided a rapid assembly, flexible and concentric mating stent tissue valve that substantially substitutes clamping for sewing, the valve comprising an inner stent, having an annular base with a plurality of posts extending from the base along an axis of the valve in the direction of blood flow, the posts being connected by a scalloped edge, and also comprising an outer stent.

The inner stent is configured with a plurality of outward extending tissue alignment members. During valve assembly, a precisely cut section or sections of tissue is prepared with a small number of small, precisely placed holes to be registered with the tissue alignment members.

These holes are configured to ensure that the resulting tissue leaflets formed in the assembled valve from the section or sections of tissue will be about the same size and shape. Next, the tissue is wrapped around the inner stent, and the holes in the tissue are registered with their corresponding tissue alignment members. These tissue alignment members will hold the tissue in place during valve assembly, to prevent circumferential, or up or down, movement of the tissue. Valve assembly is then completed by placing an outer stent over the tissue. The outer stent has integrated within it self-adjusting tensioning means, such as a garter spring or the like, which clamps the stents together while compensating for irregularities in the tissue, and secures the tissue between the stents.

The outer stent is configured to apply a uniform and self-adjusting clamping force on the tissue. To accomplish this, the outer stent is advantageously configured to mate closely with the inner stent. It is advantageously configured, as is the inner stent, with a plurality of posts extending from an annular base and connected with a scalloped edge, which posts are configured for close alignment with corresponding inner stent posts. The posts of the outer stent are advantageously tapered inward and have windows in the shape of an outline of the corresponding inner stent posts, which are adapted for alignment with the outer stent posts. As a result, when the stents are mated, the inner post stents are biased towards nesting into the outer stent posts. The result is a self-adjusting clamping force generated between the posts of the stents. Second, the annular base of the outer stent is configured with window extensions or the like which split the base of the stent in one or more places. This enables the outer stent to splay open to easily fit around the inner stent during valve assembly, without damaging the tissue. Moreover, the self-adjusting tensioning means, such as a garter spring or the like, is integrated with the outer stent by fitting it into a groove extending around the periphery of its annular base. This enables the outer stent to apply a self-adjusting clamping force to the tissue between the annular bases of the stents in response to any irregularities of the tissue at hand. The clamping force generated by the tapered and windowed stents, and by the self-adjusting tensioning means, together is sufficient to secure the tissue between the stents without substantial reliance on the tissue alignment members, whose primary role substantially ceases after the valve is assembled. This cessation of functionality of the alignment members in the assembled valve is crucial, for it prevents stress from becoming concentrated at the alignment members, which could lead to the tearing of the tissue, and premature failure of the valve.

A sewing ring is also advantageously integrated into the outer stent to provide a means for suturing the assembled valve to the annulus of the heart to be fitted with a new valve.

A standardized and reproducible method of assembling the valve in the operating room is also provided. This is accomplished through the use of a plurality of prefabricated, and possibly disposable kits, which contain all the components necessary to harvest the tissue from the patient, and then assemble the valve. A first sterile, disposable tissue harvesting and annulus sizing kit is provided which contains a roughly-sized tissue template for use in harvesting a section of tissue roughly of the appropriate size. A plurality of obturators of different sizes is also provided. The technician or surgeon successively plugs the annulus of the heart to be fitted with the obturators until the appropriate size of the annulus is determined.

An optional quick-fix kit is also provided. This kit can be provided separately, or alternatively, it can be integrated with the first kit. This kit provides a basin and a sterile supply of glutaraldehyde or the like. This kit provides means for dipping the harvested tissue into the glutaraldehyde solution, thereby quick-fixing it.

A second sterile, disposable size-specific stent and valve assembly kit matched in size to the specific annulus is then provided containing the size-specific inner and outer stents, and tools needed to assemble, test, and hold the valve. This kit contains a size specific tissue cutting die to precisely cut the tissue in the flat to an exact pattern and size appropriate for the particular annulus to be fitted, and also to cut precise holes in the tissue to be registered with the tissue alignment members on the inner stent. This die is configured so that the tissue will not require any additional trimming or processing after it is incorporated into the valve. Additional assembly tools are also provided, consisting of an assembly mandrel and outer stent spreading tools. To assemble the valve, the inner stent is placed on the mandrel, and the precisely cut tissue is then wrapped around the inner stent such that the holes in the tissue are registered with the tissue alignment members. The spreading tools are then used to spread open the outer stent, and place the outer stent over the inner stent without damaging the tissue.

Next, a valve acceptance tester is provided to test the valve before implanting it. To accomplish this, the valve is placed in the tester, and observed while a known volume of saline or the like is displaced through the valve, and then while a known back pressure is applied. If the valve is operating normally, it is then implanted in the human. To implant the valve, a valve holder is provided, for use by the surgeon when implanting the valve.

These kits pave the way for the assembly of an autogenous valve in the limited time available. The potential of these valves lies in their lack of antigenicity and potential for viability compared with animal tissue valves. As a result of their lack of antigenicity, and potential for continued viability, these valves also have the potential of being more durable compared to animal tissue valves.

These valves can be constructed with many sources of tissue, such as pericardial tissue (the tough fibrous tissue surrounding the heart), fascia lata (the tough fibrous casing around the leg muscle), and rectus sheath (the tough fibrous casing from the abdominal muscles), and others. However, pericardial tissue may be the preferred tissue because of its proximity to the heart and to the surgical procedure, and because the biological form and structure of the human pericardium is similar to that of the natural valve elements. Another advantage is that pericardium typically has an identifiable range of thicknesses and strengths, and, therefore, valves assembled with pericardial tissue are capable of being assembled with standardized components themselves constructed in accordance with uniform specifications.

DESCRIPTION OF THE PREFERRED EMBODIMENTS

The components which make up the assembled valve are illustrated in FIG. 1. As illustrated, these components consist of outer stent 1, tissue 2, and inner stent 3.

Turning first to the inner and outer stents, the inner and outer stents preferably have inner and outer stent frames, respectively, constructed out of a thermoplastic such as DELRIN or the like using injection molding techniques to form the entire component using uni-body construction techniques, instead of using welding or the like to attach any protuberances. Uni-body construction is less risky to the patient than welding since welded bonds can more easily break, leading to valve components or fragments being injected into the blood stream.

Once constructed, the outer stent frame is integrated with other components such as a sewing ring and a garter spring and both frames are covered with a fabric such as DACRON or the like, to form the completed inner and outer stents used in valve assembly.

Figure 2A:
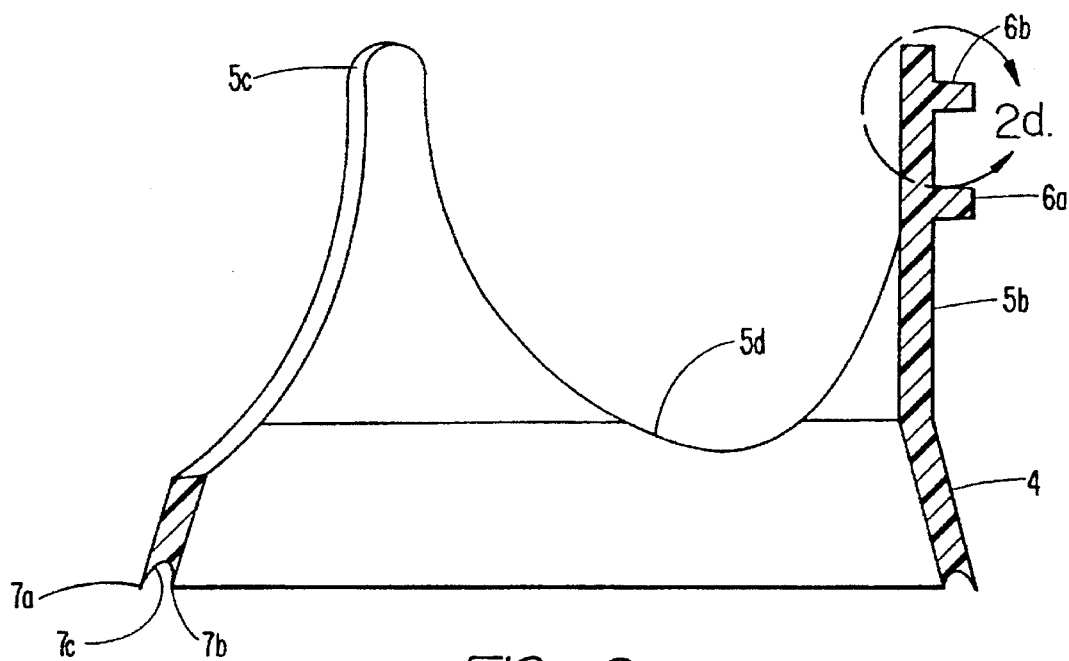
FIGS. 2a–2d illustrate, in detail, the inner stent frame.

Turning now to FIGS. 2a–2d, additional detail regarding the construction of the inner stent frame will be described. With reference to FIG. 2a, the inner stent frame is preferably constructed with an annular base 4 with a plurality of posts identified with reference numerals 5a, 5b, and 5c extending from the annular base along an axis of the valve in the direction of blood flow through the valve. Preferably, three such posts are provided which are spaced uniformly around the annular base, i.e., such that the centers of adjacent posts are separated by 120 degrees. In addition, the posts are preferably connected by scalloped walls, one such wall being identified with reference numeral 5d in the figure. As illustrated, at least one such post is initially constructed with a plurality of outward facing members 6a, 6b. Preferably, all posts will be constructed with these members. These members will later be shaped into tissue alignment members for use in holding the tissue in place while the valve is being assembled. Additional detail on one of the members, i.e., member 6b, is provided in the close-up of FIG. 2d. Note that the members, when initially constructed, are slightly tapered inward. This is a function of their being injection molded, since this tapering enables the members to more easily be removed from the respective mold. Tapering also improves the strength of the members.

The inner stent frame is also preferably constructed with a view towards eventually covering the stent frame with DACRON fabric and bonding the stent frame to the fabric. To facilitate bonding of the stent frame to the fabric, energy directors 7a and 7b are provided at the bottom of the stent frame. These directors will be used to attract ultrasonic energy, causing the thermoplastic at this specific location to melt, and bond the fabric to the stent frame. The energy directors 7a and 7b are preferably separated by notch 7c as shown. This notch is designed to consume the fabric seam of the stent sock (illustrated in FIG. 4a) once it is placed over the inner stent frame.

As illustrated, the annular base 4 of the inner stent frame is preferably tapered inward at about 5–15 degrees from the vertical. As will be discussed further on, the outer stent frame is correspondingly tapered as well. Together, this tapering facilitates nesting between the inner and outer stent frames, which nesting contributes to providing a self-adjusting clamping force over the tissue between the inner and outer stents. Furthermore, the tapering will help bias the valve into a closed position, which enables the valve to close more easily in low pressure conditions. Finally, the tapering produces a "jet nozzle" effect which reduces turbulence as blood flows through the valve, leading to a smaller net pressure drop across the valve, resulting in less energy loss to the valve. These concepts will be described in more detail further on.

Figure 2B:
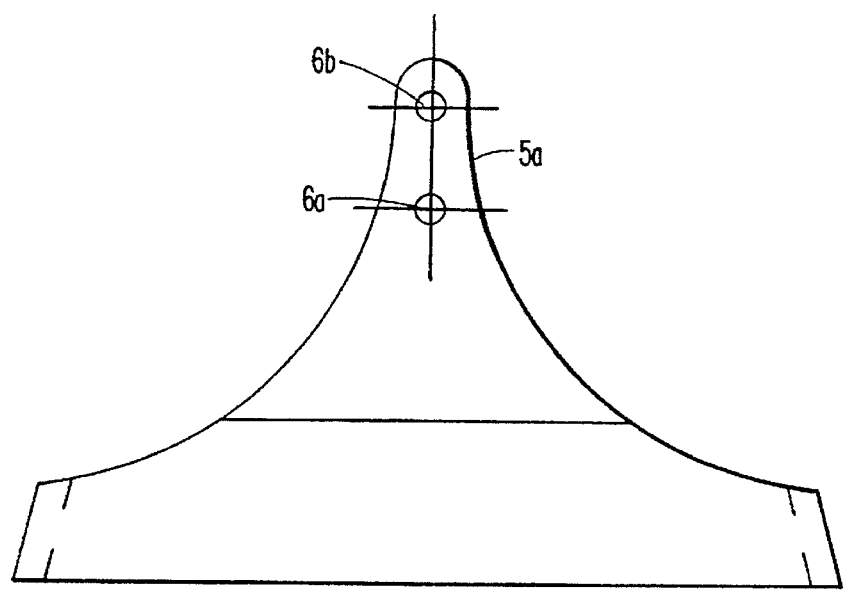
Figure 2C:
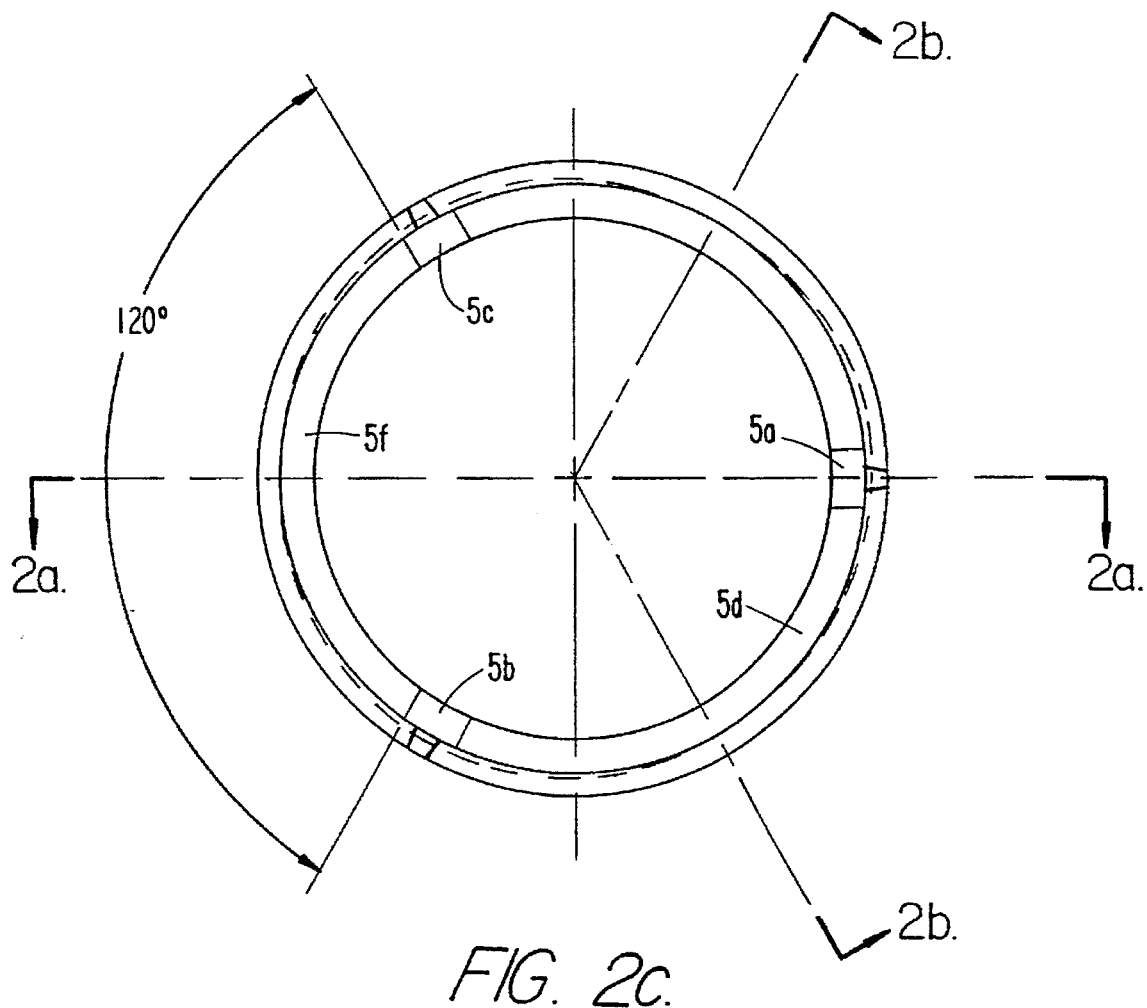
Figure 2D:
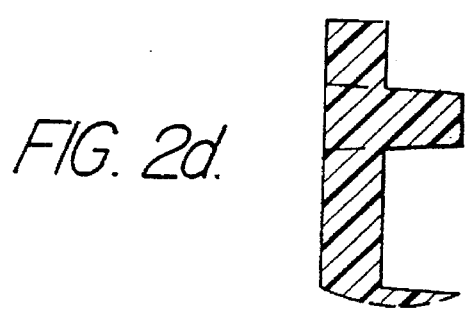

Turning now to FIG. 2c, this figure illustrates a top view of the inner stent frame. As illustrated, in the preferred embodiment, three approximately equally spaced posts 5a, 5b, 5c protrude from the annular base, with scalloped edges connecting the posts. However, it should be appreciated that other examples are possible, including where the posts are unequally spaced, and where more or less than three posts extend from the base.

Turning now to FIG. 2b, this figure illustrates a side view of the inner stent frame of FIG. 2c. A cross-sectional side view of FIG. 2c was previously provided in FIG. 2a. As illustrated, in the preferred embodiment, each post is constructed with two outward-facing members 6a and 6b. Again, however, it should be appreciated that other examples are possible, such as where each post is constructed with more or less than two outward facing members, where only some of the posts are constructed with outward-facing members, or where the annular base is constructed with outward-facing members. All these examples are intended to be included with the scope of the invention. As will be described in more detail further on, these members will ultimately be formed into the tissue alignment members which are designed to position the tissue in place on the inner stent and prevent its movement during valve assembly.

Figure 3:
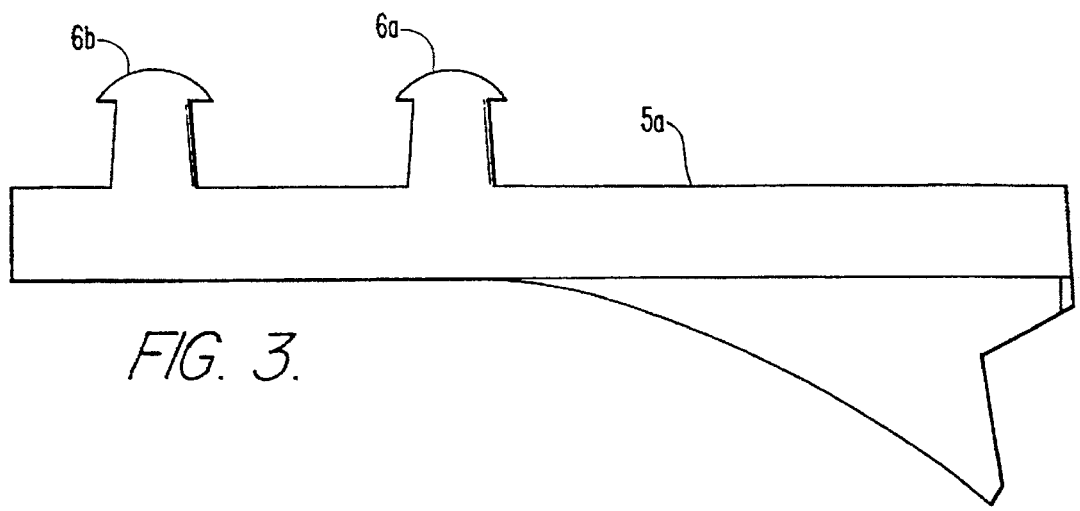
FIG. 3 illustrates, in detail, the tissue alignment numbers of the inner stent.

After the inner stent frame is formed, the outward-facing members formed on the stent frame are next processed into tissue alignment members such as hooks, barbs, or members with mushroom capped ends or the like. FIG. 3 illustrates tissue alignment members 6a and 6b configured as mushroom-capped members. Preferably, the members are shaped to have mushroom caps. This is accomplished by directing radiation from an energy source, such as conventional heat, impulse heat, ultrasonic energy, or the like, to deform the heads of the members into a mushroom shape. A preferable energy source is ultrasonic energy, since it can be applied in a controlled manner to form the mushroom heads, but other sources are possible.

Before or after formation of the mushroom heads, the stent frame is covered with fabric such as DACRON or the like, such that the tissue hooks protrude through the fabric. As mentioned briefly earlier, covering the stent frame accomplishes the purpose of isolating non-biological material, such as the thermoplastic of the stent frame, from the body. This helps avoid the problem of thromboembolism, which occurs with the use of mechanical valves. It also accomplishes the purpose of promoting tissue ingrowth into the interstices of the fabric, to further isolate the non-biological material from the body, and integrate the valve into the heart. Additionally, it accomplishes the purpose of providing an interface to the tissue clamped between the stents which is gentle, and which helps nourish the tissue and promote its viability by allowing free passage of blood to the tissue.

To cover the inner stent frame, first, a three-fingered DACRON sock or glove is formed by heat seaming sections of DACRON fabric together utilizing either hot wire or ultrasonic techniques. Alternatively, the entire glove can be woven as one piece. The glove is then pulled over the stent frame, and secured with a heat seam at the base of the glove. The seam and surrounding fabric are then thermally-bonded to the base of the stent frame utilizing the energy directors 7a and 7b illustrated in FIG. 2a, in conjunction with ultrasonic energy. Other sources of heat and/or pressure are possible, but ultrasonic energy is preferable, since the melt distance, and molten thermoplastic flow into the fabric interstices, can be accurately controlled and repeated in a production environment with ultrasonic energy.

Figure 4A:
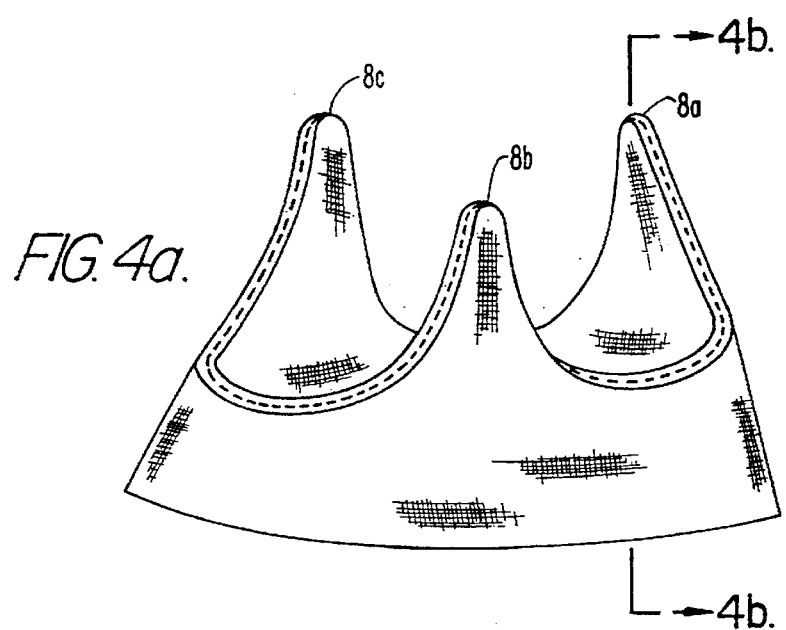
FIGS. 4a–4b illustrate the stent sock.

Turning now to FIG. 4a, additional detail on the stent sock is provided. The three-fingers of the sock, which will fit over the three posts of the inner stent frame, are identified with reference numerals 8a, 8b, and 8c. Since the inner stent frame will preferably be manufactured in a variety of sizes, configured depending on the annulus of the heart to be fitted, it is desirable to be able to manufacture the stent sock, as well, in a corresponding variety of sizes. At present, stent socks have been produced in sizes ranging from 14 mm–20 mm, although other sizes are possible. It has been found that this range of sizes is acceptable for use with the inner stent frame sizes of 19–31 mm since the DACRON fabric can easily be stretched to fit over the nominally larger inner stent frame. Moreover, the stent sock is preferably constructed from knitted DACRON tube similar in weave to implantable large vessel grafts. Both tubular and flat DACRON are possible.

Figure 4B:
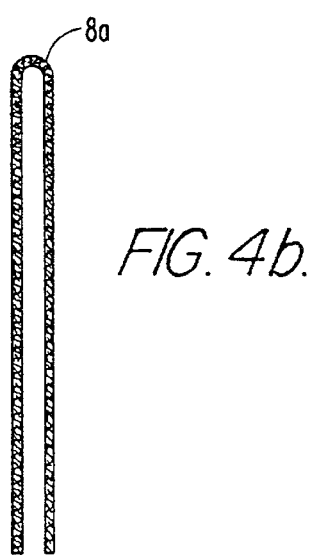

Turning now to FIG. 4b, this figure illustrates a cross-sectional portion of the stent sock used to cover one of the stent posts, identified with numeral 8a in the figures.

Figure 5A:
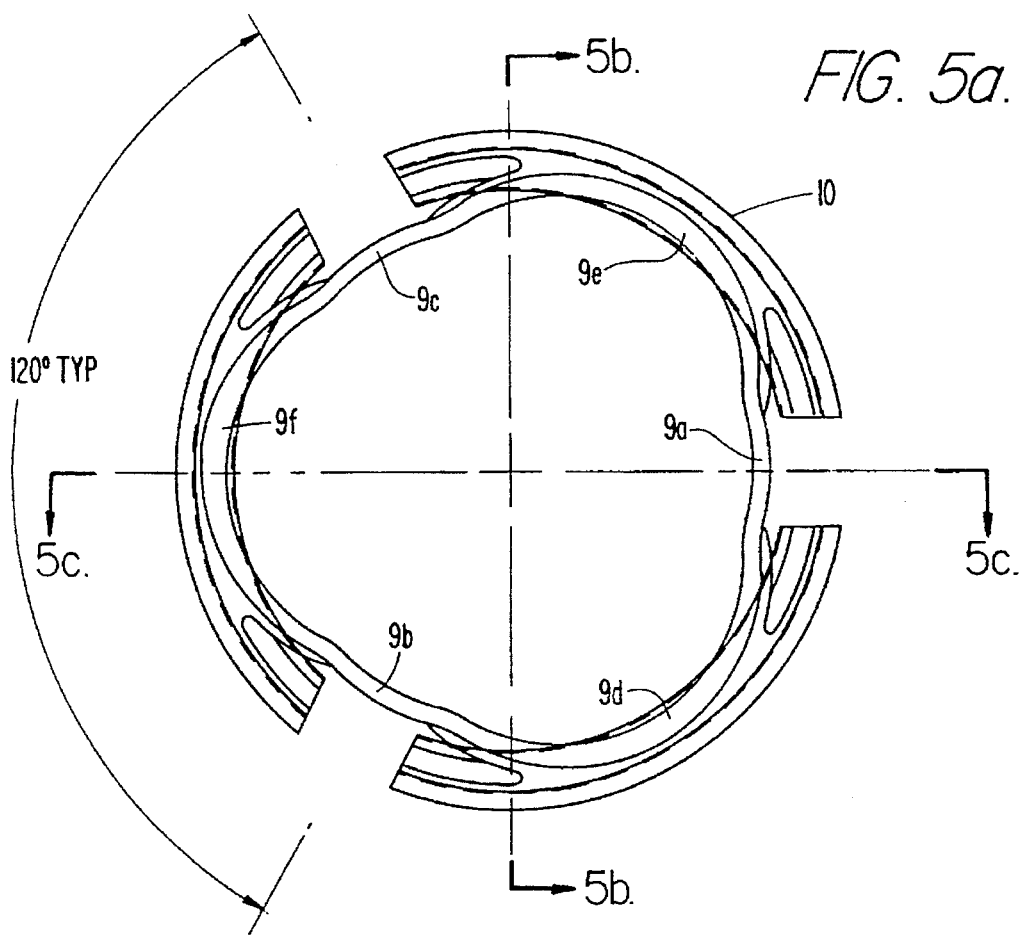
FIGS. 5a–5d illustrate, in detail, the outer stent frame.
Figure 5B:
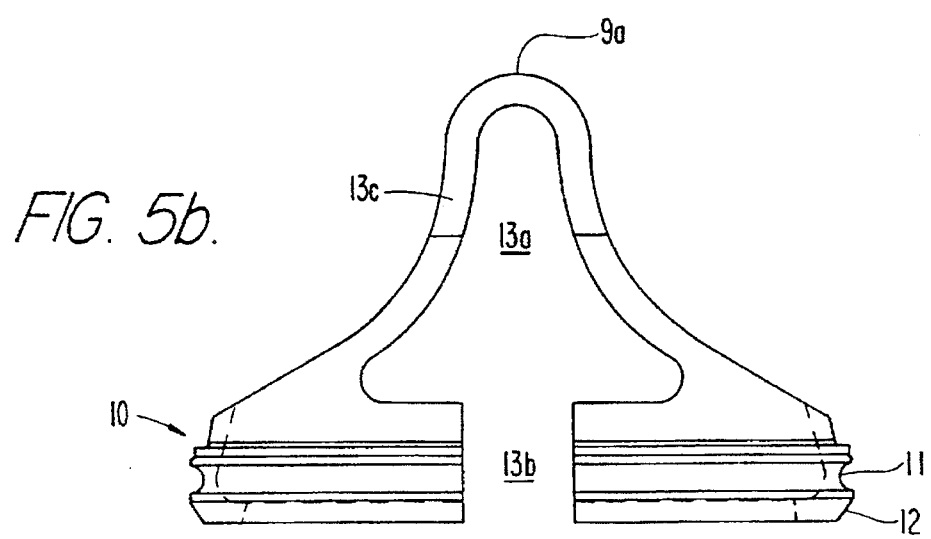
Figure 5C:
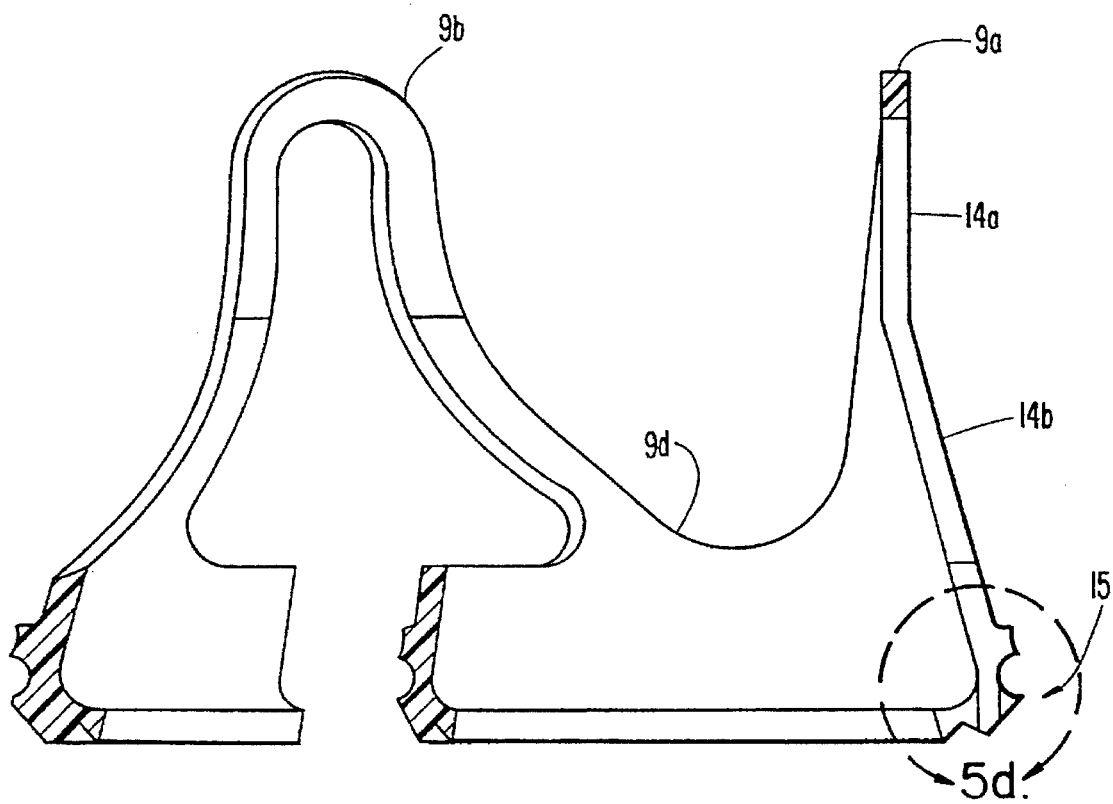

Turning now to the outer stent, additional detail on the outer stent frame is illustrated in FIGS. 5a–5d. A top view of the outer stent frame is illustrated in FIG. 5a. As illustrated, the outer stent frame preferably has a similar construction as the inner stent frame, in that the outer stent frame preferably has an annular base 10, and three equally spaced posts, 9a, 9b, and 9c, protruding from the base along an axis of the valve in the direction of blood flow, and connected by a scalloped edge. One such edge, identified with reference numeral 9d, is shown in FIG. 5c, connecting posts 9a and 9b.

A side view of the outer stent frame is illustrated in FIG. 5b. This figure illustrates additional aspects of the outer stent frame. As illustrated, the annular base 10 is preferably constructed with a groove 11 around the periphery of the outer stent into which self-adjusting tensioning means such as a garter spring or the like will eventually be fitted. In addition, a flange at the bottom of the annular base, identified with reference numeral 12, is provided with an inward taper to facilitate locking the outer stent over the inner stent. Eventually, this flange will be used to lock under the bottom of the annular base of the inner stent to ensure a tight fit between the stents.

Another aspect of the outer stent are the windows in the posts. Preferably, each post is configured with a corresponding window, and one such window, identified with reference numeral 13a, is shown for post 9a in FIG. 5b. As shown, the window generally defines a contour in the corresponding post, in this instance post 9b, of the outer stent frame, and is surrounded by a member 13c which gives the shape of the post. Preferably, one such window is contained in all the posts of the outer stent frame, although examples are possible where not all the posts are constructed with windows. As will be discussed in more detail further on, the window is designed to facilitate nesting between the inner and outer stents. When the outer stent is eventually placed in a close mating position with the inner stent, the posts of the outer stent are preferably situated so as to coincide with the posts of the inner stent. To facilitate nesting, the windows should be large enough to accommodate the posts of the inner stent, and should generally follow the same contours as the inner stent posts. During valve assembly, as will be discussed in detail further on, this nesting will provide a self-adjusting clamping force on the tissue between the stent posts.

A further aspect of the outer stent frame is window extension 13b, illustrated in FIG. 5b, which extends through the annular base of the outer stent. As shown, the window extension extends from the window 13a and through the portion of the annular base below the window. Preferably, one such extension is contained in every post of the outer stent, although other examples are possible, such as where only some of the posts contain window extensions, or where the window extensions are replaced by slots which split the annular base at positions along the annular base below the posts. As will be discussed in more detail farther on, these extensions or slots enable the outer stent to be spread open so that it can be easily fitted over the inner stent without damaging the tissue during the valve assembly process.

Further aspects of the outer stent frame are illustrated in FIG. 5c, which is a cross-sectional view of the illustration in FIG. 5a. As illustrated in FIG. 5c, post 9a of the other stent frame is preferably comprised of two segments 14a and 14b. The bottom segment 14b is preferably tapered inward at an angle of about 5°–15° from the central dimension, whereas the top segment 14a, is preferably straight. Preferably, each of the posts of the outer stent frame are configured in like manner.

This tapering configures the outer stent to fit closely with the inner stent, which, as discussed previously, is similarly tapered. Moreover, this tapering serves additional purposes, including producing the jet nozzle effect, and biasing the valve into a closed position.

A further aspect of the outer stents are the energy directors 15. These serve the same purpose as the energy directors of the inner stent: They serve to attract energy, preferably ultrasonic energy, enabling the thermoplastic in the immediate vicinity of the director to melt in a controlled manner.

Figure 5D:
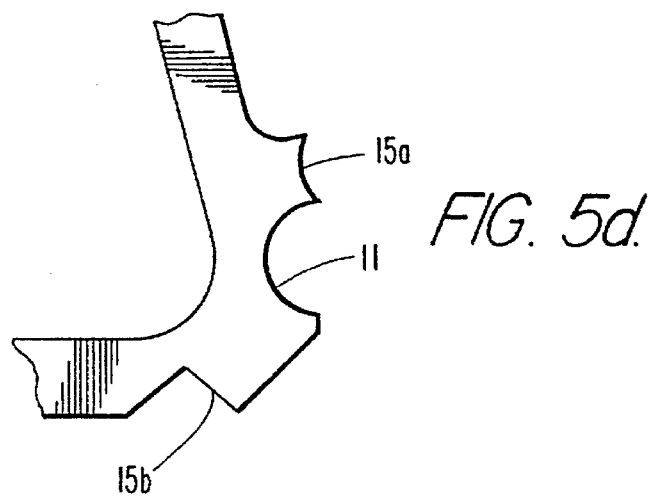

Further detail on the energy directors is provided in FIG. 5d. As illustrated, the energy directors extend around the periphery of the annular base, and consist of thermoplastic formed into sharp corners. One such director, identified with numeral 15a, extends around the top of the annular base, while the other, identified with reference numeral 15b, extends around the bottom of the annular base. The groove 11 in the annular base, previously described, is situated between the two directors.

As with the inner stent frame, the outer stent frame is preferably injection molded out of a thermoplastic such as DELRIN or the like, and then covered with a DACRON stent sock, which is then closed with a heat seam at the base of the stent. Then, the sock is thermally-bonded to the stent upon the application of heat and pressure, which is preferably applied through the application of ultrasonic energy. The placement of the energy directors is such that the DACRON fabric will be bonded to the outer stent frame along two concentric seams on either side of the notch.

Other variants of the outer stent frame are possible. In one variant, the outer stent frame is a composite structure, whereby the posts of the stent frame are manufactured using a spring alloy metal such as MP 35N, ELGILOY, 17-7PH Stainless, or the like, while the annular base of the stent frame will continue to be made from thermoplastic. The benefits of this composite structure are that the overall mass of the outer stent posts is reduced, and in addition, the manufacturability of the outer stent frame may be improved, and provide even greater control of the outer stent clamping.

It should be appreciated that the outer stent frame can be integrated with other components before it is covered with the stent sock. In the preferred embodiment, for example, the outer stent frame is integrated with a elastomeric collar and self-adjusting tensioning means before it is covered with the stent sock. Together, these components define the outer stent identified with numeral 1 in FIG. 1. Preferably, the self-adjusting tensioning means is a garter spring, which floats in the outer stent groove, but it can be any other helically wound wire or the like. The spring is preferably made out of a material such as MP-35N, a cobalt nickel-chromium and molybdenum alloy, or the like, and other materials are possible provided that the material has good biocompatibility, has high strength, and can produce a known, constant and evenly distributed clamping force. For example, elastomer rings are possible since they meet these criteria. Additional detail on the garter spring is provided in FIGS. 5e–5h. The spring is advantageously coiled at 7 mils/coil, with a diameter of about 38 mils for each coil. The spring is formed out of a wire coil, where the spacing between the coils is advantageously equal to the diameter of the wire. As illustrated in FIG. 5h, the ends of the spring are advantageously connected simply by screwing them together. The length of the spring should be such as to accommodate the outer diameter of the outer stent. It should be appreciated that these dimensions can change with valve size.

The outer stent is assembled by placing the garter spring or the like into the groove 11 in the annular base of the stent frame, followed by placing the elastomeric ring around the garter spring. The elastomeric ring is preferably made of silicon or the like, although other examples are possible, provided that the material used is flexible, resilient, and has relatively high strength. Then, the DACRON stent sock is thermal-bonded to the thermoplastic frame in the manner described previously. The result is an integrated structure which is flexible enough to be spread open wide enough to fit easily over the inner stent, while also being capable of retracting automatically to apply a self-adjusting clamping force to the tissue between the stents. The self-adjusting aspect of the clamping force is beneficial; it enables the tissue to be clamped without slippage even though the thickness of the tissue used may vary, depending on the individual patient, and in addition, despite irregularities in the tissue itself which may cause the thickness to vary within the piece of tissue.

The elastomeric ring, when covered with the DACRON fabric, will serve as a sewing ring in the completed valve assembly. Specifically, this ring will be the vehicle for sewing the assembled valve into the annulus. The garter spring and elastomeric ring cooperatively interact, in that if the garter spring breaks for any reason, the integrity of the valve will be maintained by the elastomeric ring, which will act as back-up to the spring. The elastomeric ring will also help prevent the garter spring from slipping out of its groove. As a result, the valve will retain its shape, retaining the inner stent, and will not catastrophically fail under these circumstances.

Turning now to FIGS. 6a–6d, these figures illustrate the two stents after the outer stent has been placed over the inner stent, to be concentric with it, with the posts of the two stents aligned. As illustrated, the configuration of the stents is such that the posts of the inner stent nest into the corresponding windows of the posts of the outer stent. This nesting does not, in fact, completely occur in the assembled valve however, since in the assembled valve, tissue will be placed between the posts, preventing complete nesting. In the assembled valve, the posts will attempt to nest with each other, but will be prevented from completely doing so by the tissue. This tendency towards nesting is beneficial, since it will provide a self-adjusting clamping force on the tissue between the stent posts, leading to less slippage, and therefore better matching of the co-aptive edges of the tissue leaflets. Another benefit is that the tissue between the stents will be more uniformly clamped in that the tissue between the posts will be securely clamped as well as the tissue between the annular bases.

Uniform clamping is beneficial for several reasons. First, it further reduces stress which may otherwise concentrate at the tissue alignment members. Second, if the tissue were to be formed by suturing a number of smaller pieces of tissue together, instead of just a single piece of tissue, uniform clamping helps relieve stress from these sutures as well. The result is a prolongation of the valve life.

For illustrative purposes, in FIGS. 6a–6d, the nesting between inner stent post 5a and outer stent post 9a is shown. It should be appreciated, however, that in the preferred embodiment, each post of the inner frame will nest with a corresponding post of the outer frame. Also shown, in cross section, is garter spring 16 which is wrapped around the annular base of the outer stent frame. Finally, elastomeric collar 17 of the integrated sewing ring is also shown in cross-section.

As illustrated, the tapering of the annular bases of the inner and outer stent posts appropriately positions the windows of the outer stent posts with respect to the inner stent posts to facilitate nesting. In fact, the taper is such that the diameter of the inward-facing surface of the top of the posts of the outer stent is approximately the same as the diameter of the outward-facing surface of the top of the posts of the inner stent. This condition ensures that this nesting takes place. This nesting provides an inherent self-adjusting clamping force which will be used to clamp the tissue uniformly between the posts.

Several physical dimensions are critical to the proper functioning of the valve. These dimensions are identified with reference numerals 18, 19, and 20 in FIG. 6c, and numeral 100 in FIG. 6b.

With respect to the dimension identified with numeral 18, this dimension is the nominal distance between the mated stents along a channel which extends down the sides and along the bottoms of the stents. It has been found that for pericardial tissue, the dimension is preferably about 0.020 inches, in order to accommodate the thickness of the tissue and the thicknesses of the DACRON fabric coverings, although for other tissue types such as fascia lata, other dimensions may be preferable.

The distance is only nominally 0.20 inches, however, since in the assembled valve, the actual distance will depend on the thickness of the actual tissue used. The self-adjusting tensioning means will cause this distance to expand or contract, in response to the specific tissue thickness, in order to generate a self-adjusting clamping force on the tissue.

As discussed earlier, the benefit of the self-adjusting attribute of the clamping force is less slippage and better stress distribution. Another benefit is that the tissue will be squeezed into the interstices of the DACRON fabric covering the stents. This results in even less slippage of the tissue.

Turning to the next critical dimension, identified with numeral 19, this dimension is the clearance between the bottom of the annular base of the inner stent and the top surface of the flange of the outer stent. As indicated, this dimension helps define a continuation of the same channel, discussed earlier, defined by dimension 18. As with dimension 18, for use with pericardial tissue, this dimension is preferably nominally about 0.020 inches, although other dimensions may be more appropriate for other tissues. It should be noted that the tissue in the assembled valve will normally extend down to point 21, at which point, the pre-cut edge of the tissue will terminate.

Turning to the next critical dimension, identified with numeral 20, this dimension is the clearance between the bottom of the window in the outer stent post and the top of the corresponding inner stent post. This dimension should be large enough to accommodate double the thickness of the DACRON fabric that is used to cover the stents, but does not have to accommodate the thickness of the tissue, since the tissue does not pass between the bottom of the window and the top of the inner stent post. However, since a seam in the fabric typically runs along the upper scalloped edge of the inner stent, this dimension should also be large enough to accommodate this seam.

Figure 6A:
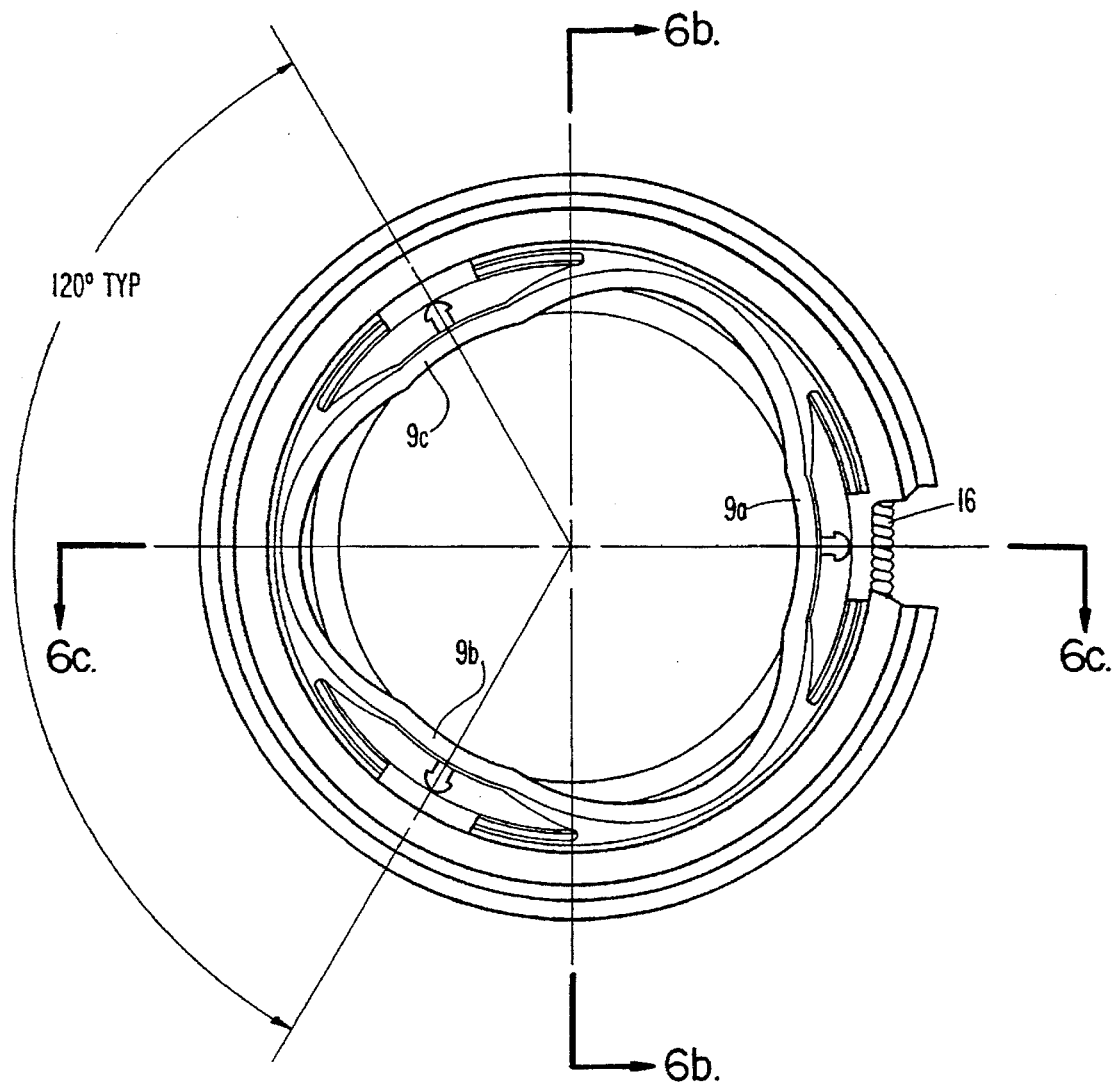
FIG. 6a–6d illustrate the stents when placed in a close mating position.
Figure 6B:
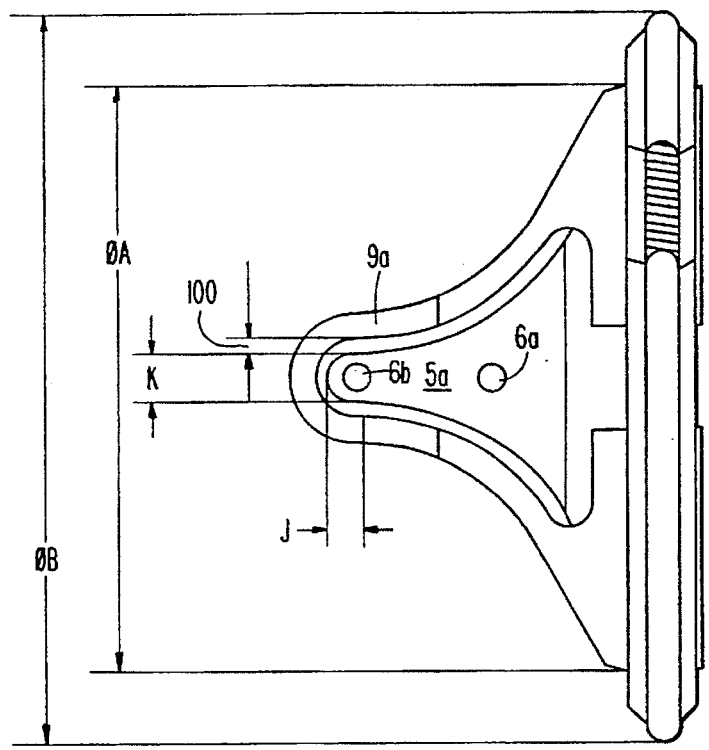

Turning next to dimension 100 in FIG. 6b, this dimension is the clearance between the inner stent post and the struts which form the window in the outer stent post. This dimension is typically 20 mils, but, as with the dimension identified with numeral 20, can vary with valve size, and only needs to be large enough to accommodate double the thickness of the DACRON fabric used to cover the stents.

Figure 6C:
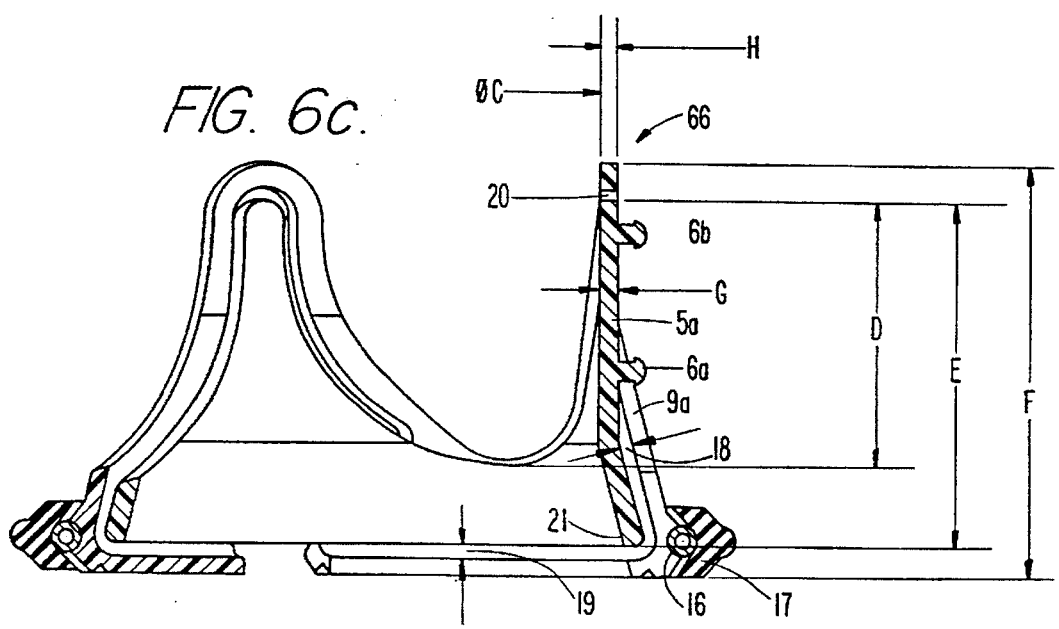

Finally, other dimensions are identified with the letters A–K, in FIGS. 6b–6c. These dimensions are proportionate to the size of the annulus to be fitted with the valve. The following table shows the preferable relationship between these dimensions (in inches) and a variety of possible sizes of the annulus to be fitted:

TABLE I

| ANNULUS SIZE | A | B | C | D | E | F | G | H | J | K |
|---|---|---|---|---|---|---|---|---|---|---|
| 19 mm | .748 | .90 | .540 | .352 | .415 | .500 | .025 | .020 | .043 | .055 |
| 21 mm | .827 | .98 | .594 | .370 | .455 | .554 | .027 | .023 | .045 | .058 |
| 23 mm | .905 | 1.06 | .651 | .405 | .500 | .595 | .030 | .025 | .050 | .060 |
| 25 mm | .984 | 1.14 | .708 | .442 | .545 | .645 | .037 | .030 | .055 | .063 |
| 27 mm | 1.063 | 1.22 | .764 | .477 | .585 | .695 | .040 | .035 | .060 | .065 |
| 29 mm | 1.142 | 1.30 | .821 | .512 | .630 | .745 | .045 | .040 | .065 | .068 |
| 31 mm | 1.220 | 1.38 | .877 | .547 | .675 | .795 | .050 | .045 | .070 | .070 |
| TOL. | –.040 | +.040 | –.005 | +.005 | +.005 | +.005 | –.003 | +.002 | +.005 | –.005 |

It should be emphasized that other valves sizes are possible such as valves configured for young children, where the annulus size might be as small as 14 mm.

The dimensions in Table I above have proven to be acceptable in practice. In other words, valves formed from components fabricated with these dimensions have proven to operate successfully.

These dimensions should, however, be as close as possible to dimensions determined from a theoretical ideal. In the theoretical ideal, these dimensions should preferably stand in certain relationships to each other, which relationships can be mathematically defined by two ratios. The first ratio can be expressed as follows:

$$((\pi/3)*(C-K))/(C-G)$$

The values of dimensions C, K, and G should be such that the ratio above is close to 1. Intuitively, this ratio is the ratio between the length of the tissue in a cusp of the assembled valve which is free to move, to the length of tissue required for the valve to close. If the ratio is less than one, the valve will not completely close, although it will close responsively. If the ratio is greater than one, this means excess tissue will be available with risk of prolapse, stress lines, excessive central droop under load, and uneven distribution of tension throughout the cusp.

Figure 6D:
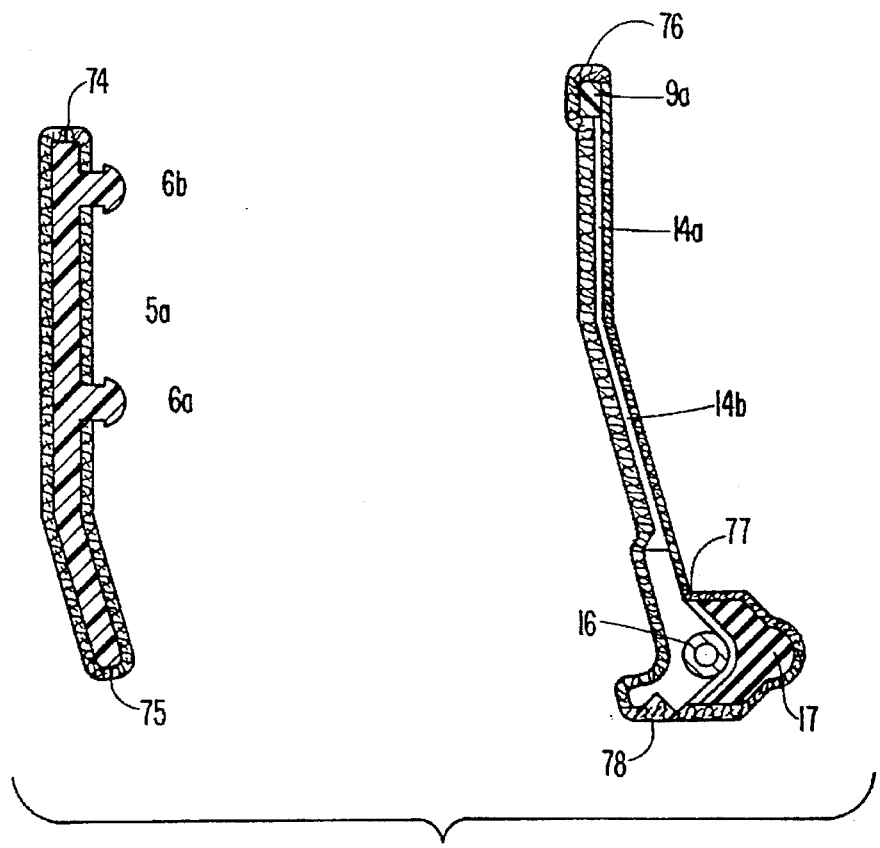
Figure 6E:
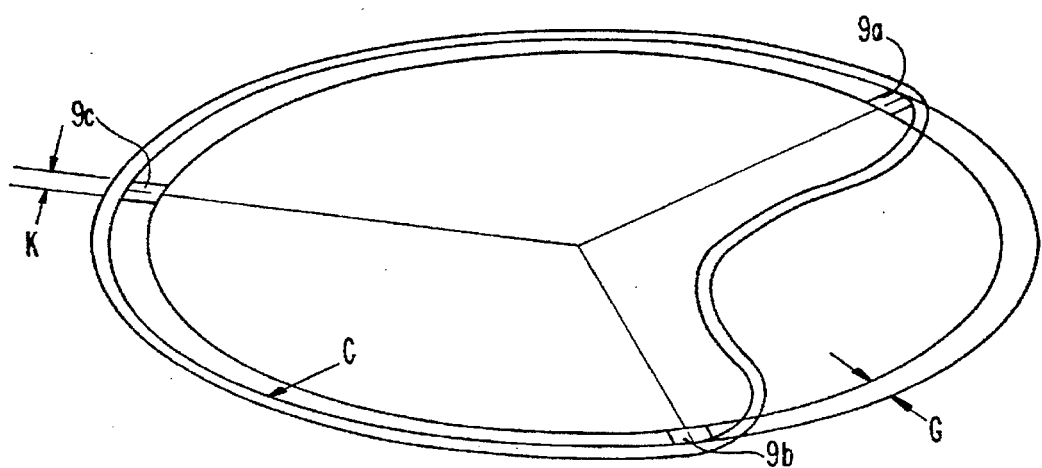
FIG. 6e–6g illustrate theoretical ideals for valve dimensions.

This ratio is further illustrated with the aid of FIG. 6e, which shows a top view of the assembled valve. These dimensions C, G, and K, used to form the ratio, are also illustrated.

Focusing for the movement on a single cusp, the length of tissue required for the valve to close will be given by twice the inside radius minus the width of the post tops, which can be expressed as C-G. The tissue that is free to move, by contrast, is ⅓ of the circumference of the cylinder formed by the tissue, with an adjustment made for the tissue situated behind the top of the posts of the inner stent, which, in fact, is not free to move. This value can be expressed as $\pi/3 *(C-K)$.

It should be appreciated that the preferred value of this ratio depends on the type of tissue used in the valve, taking account of any observed or predicted shrinkage, or stretching. The ratio should be varied according to the long term behavior of the tissue in situ. For example, fascia lata stretches more than pericardium. Hence, for fascia lata, the preferred value of this ratio should be different from that for pericardium to account for this stretching. It may also vary with the material used to form the stents. In addition, since bovine pericardium has been observed to stretch quite a bit, a valve designed for use with bovine pericardium should be designed with a ratio smaller than 1. This stretching may not occur with viable tissue, such as human pericardium, which may even shrink. Hence, with human pericardium, the ratio may even be greater than one. Moreover, it may be advantageous to build slight redundancy into the valve. This can be accomplished by designing a valve configured for a ratio slightly greater than one. Such a valve would model the native valve, which is configured by nature with slight redundancy.

The second ratio can be expressed as follows:

$$2*(D-J)/C$$

The values of the dimensions C, D, and J should also be such that the second ratio is as close as possible to 1. Intuitively, this ratio defines the geometry of a vertical centerline profile of a cusp when the valve is in a closed position, without any pressure being exerted on the valve. A spherical geometry for the centerline profile is preferred, since geometries other than this will yield a valve which is too tall or too short. If the valve is too short, even though it may be characterized as being low profile, the valve now has less stent profile to distribute stress to. If the valve is too tall, it will have all of the attendant problems associated with that characteristic.

Figure 6F:
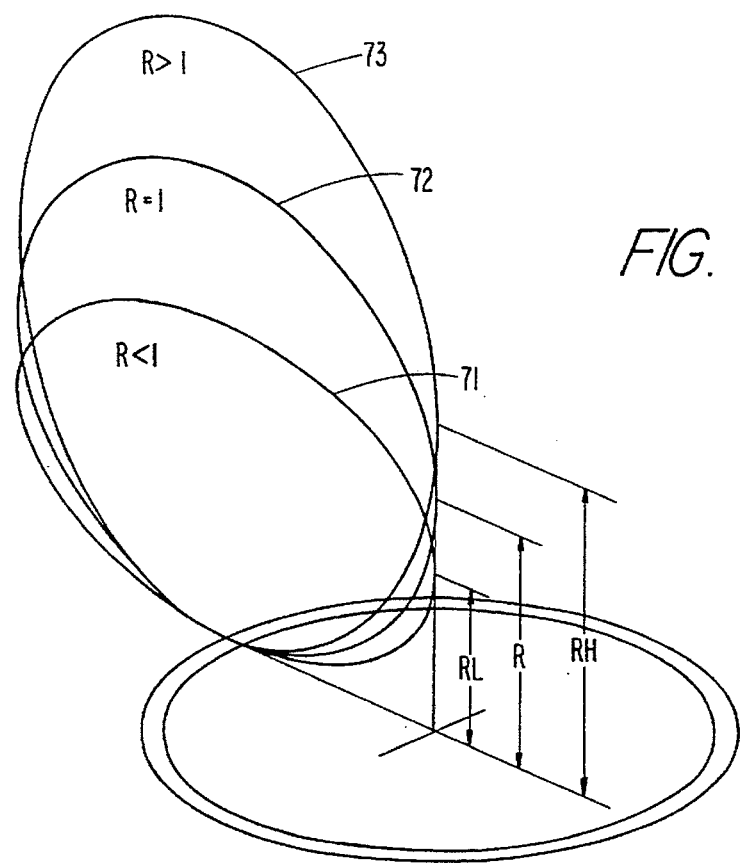
Figure 6G:
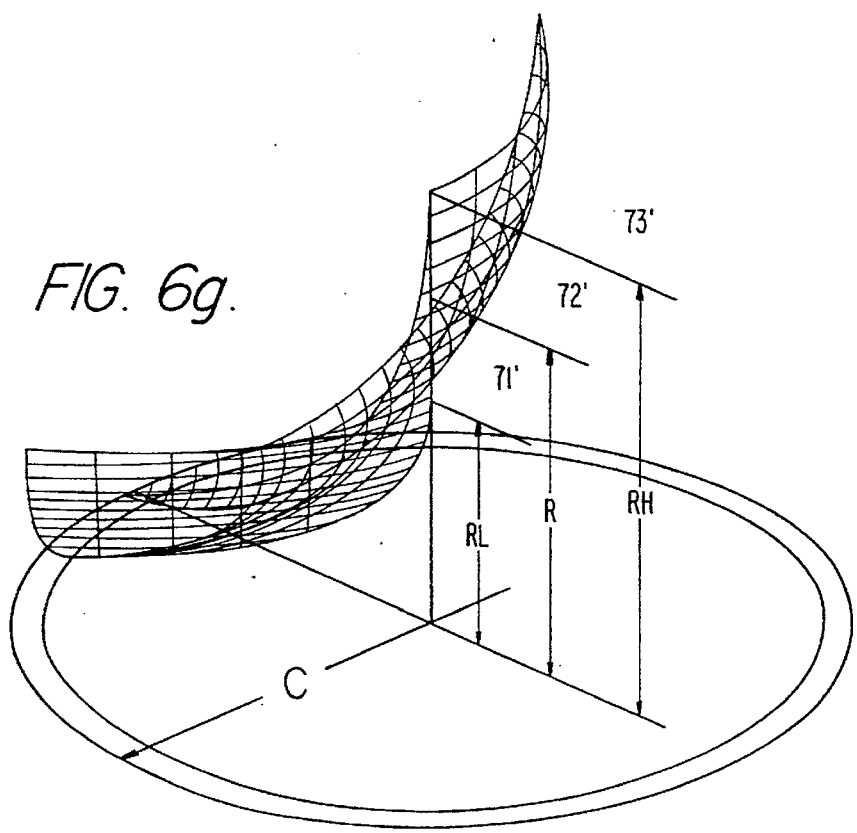

This ratio is the ratio between the height of the tissue in a cusp which is free to move, which can be expressed as D-J, to the inside radius of the valve, which can be expressed as C/2. If this ratio is equal to 1, the centerline profile of the cusp will approximate a spherical shape, whereas if the ratio is greater or less than one, the centerline profile will approximate an elliptical shape. If the ratio is greater than one, the valve may be too short for adequate stress distribution, while if the ratio is less than one, the valve may be too tall. A spherical shape yields a valve which provides adequate stress distribution, while avoiding the problems associated with a too tall valve. This ratio can be further explained using FIGS. 6f–6g. FIG. 6f illustrates the geometry of the centerline profiles for the valve, 71, 72, 73, where the ratio is, respectively, less than 1, equal to 1, and greater than 1. As shown, only the profile where the ratio is equal to 1 yields a spherical geometry. FIG. 6g is similar to FIG. 6f, except that here, the geometry of the centerline profile is shown in three dimensions. The geometries when the ratio is less than 1, equal to 1, and greater than 1 are identified, respectively, with reference numerals 71', 72', and 73'.

The practical dimensions of Table I are substantially close to the theoretical ideal. The value of these first ratio, computed using these dimensions, is about 0.997 for all valve sizes listed in the table, while the value of the second ratio, computed using these dimensions, is about 1.081, again, for all valve sizes listed in the table.

Turning to FIG. 6d, this figures illustrates a cross-sectional view of both the inner and outer stents, the inner stent on the left, and the outer stent on the right. Turning to the inner stent, the DACRON sock is advantageously seamed along the top 74, and along the bottom. Only seam 75, however, in this example, is bonded to the stent frame using ultrasonic energy or the like. Turning to the outer stent, the DACRON sock covering this stent is advantageously seamed along the top 76 and the bottom 78. Again, however, in this example, only the bottom seam 78 is bonded to the stent frame. Moreover, in this example, the sock is also bonded to the frame along perimeter 77, just above the sewing ring, but the sock is not seamed there.

Turning now to the tissue 2 in FIG. 1, this tissue is preferably autogenous tissue, such as pericardial tissue, but it may also be fascia lata, rectus fascia (or sheath), or vein tissue. These tissue sources are all relatively flimsy and difficult to handle. This is because this tissue once harvested will have a thickness of about 10-12 mils. By comparison, bovine pericardium is about 15-20 mils thick. Therefore, as will be described in more detail further on, after the tissue is harvested, the tissue is usually quick-fixed by dipping it in 0.6% glutaraldehyde solution. This serves to toughen it, and make it easier to handle.

In addition, other tissue sources besides autogenous tissue are possible, such as bovine pericardium or other xenograft tissue or the like. Further, homograft tissue is possible. These tissues could be pre-cut by the valve builder or valve manufacturer outside the operating room, and then stored via conventional methods. If these other tissue sources are used, however, the critical dimensions, identified with numerals 18, 19, and 20 in FIG. 6c, may need to be adjusted accordingly so that this tissue, which is generally thicker than the preferred tissue sources, can be accommodated.

It should be appreciated that in the assembled valve, the tendency towards nesting of the posts ensures that the tissue situated between the stent posts and along the scalloped edge between the posts will be securely and uniformly clamped. Moreover, it should also be appreciated that the tissue situated between the annular bases of the stent will also be securely and uniformly clamped between the stents by the action of the garter spring. Together, this clamping helps ensure that stress will be distributed more uniformly throughout the valve, compared to the use of non-clamping means to secure the tissue, or compared to clamping concentrated just along the annular bases. In the former case, mechanical fixation points will be created at which stress will be concentrated. In the latter case, stress will be concentrated at the tissue along the annular bases. It should be appreciated, moreover, that due to this clamping, the tissue alignment members, after valve assembly, will not constitute mechanical fixation points. Instead, their primary role will be limited to tissue alignment during valve assembly. This is important, since, as discussed above, stress tends to concentrate at mechanical fixation points. Clamping, by contrast, helps maintain uniform stress distribution, and extend valve durability.

Turning now to a method of assembling the valve, the valve is capable of being assembled in the operating room from one or more preassembled, sterile, and disposable kits. A first kit, a tissue harvesting and annulus sizing kit, is not dependent on the size of the annulus being fitted, and provides means to harvest a tissue rectangle which is large enough to be used with all size valves, means to clean and fix the tissue, and also means to size the annulus. Alternatively, a separate kit could be provided with means to clean and fix the tissue. This separate kit could have applications in separate surgical procedures such as repair of native valves. When these steps are accomplished, a second kit comes into play.

The second kit is dependent on the size of the annulus being fitted. It provides means to cut the tissue rectangle into the appropriate pattern and size required, it provides the size-specific inner and outer stents, and it also provides means to assemble the components and tissue together to arrive at the assembled valve, adapters for mounting the assembled valve in a tester to test the valve before implantation, and a holder to hold the valve during implantation. The tester itself could also be provided in this kit, instead of just the adapters, or alternatively, the tester could already be provided in the operating room.

Figure 7A:
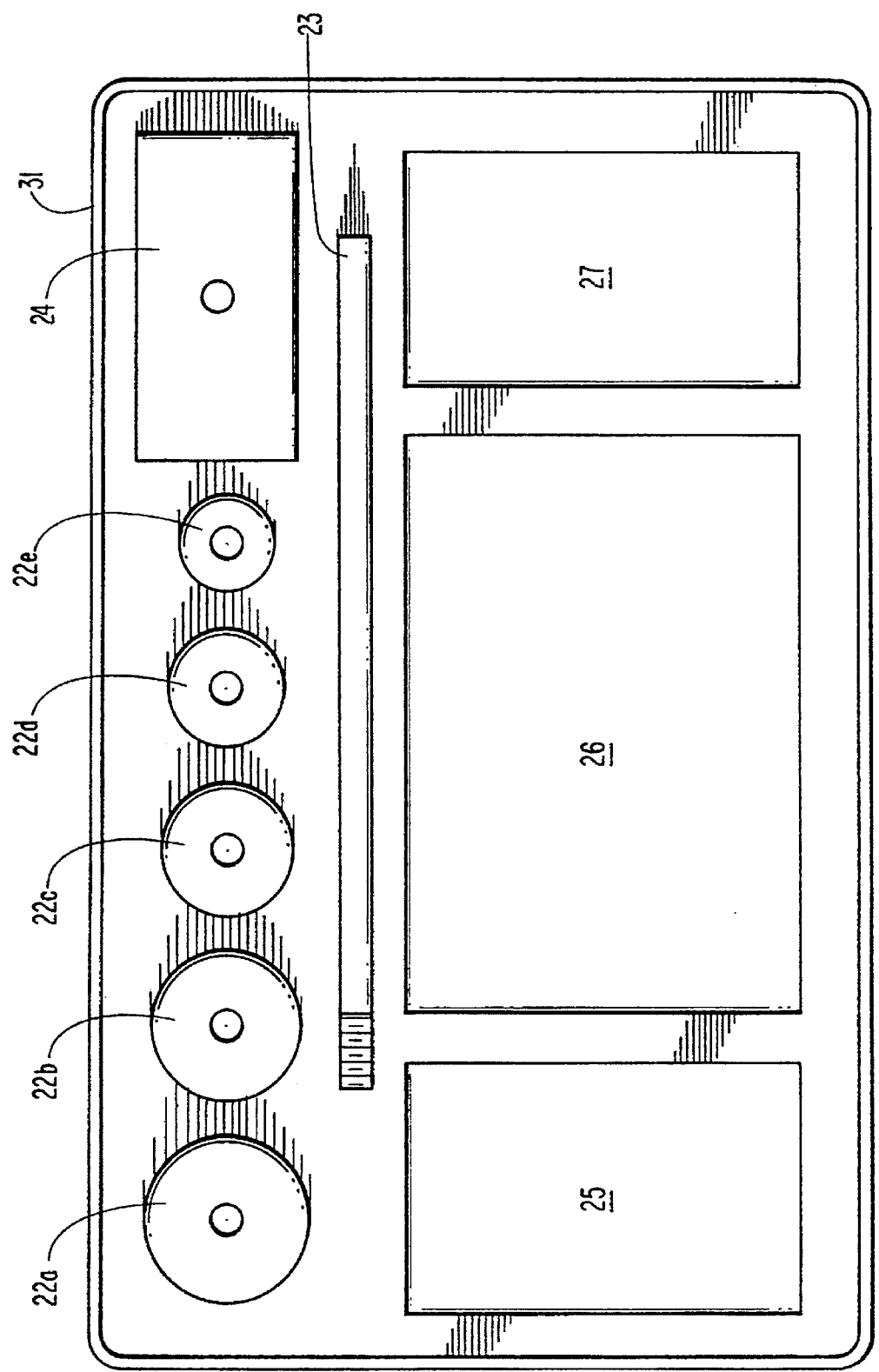

An example of a tissue preparation and annulus sizing kit is illustrated in FIG. 7a. Different kits will be provided for the atrioventricular valve positions (the mitral and tricuspid valves), and for the aortic/pulmonary valve positions. The particular example illustrated in FIG. 7a is a kit for an atrial/ventricular valve. The components in this kit will now be described, and the differences between this kit and kits for aortic/pulmonary valves will be noted.

Tissue template 24 is a rough sizing template, which the surgeon utilizes to ensure that an adequate amount of tissue is harvested, whatever the ultimate valve size turns out to be. To accomplish this, the surgeon will also utilize universal handle 23. First, the surgeon will screw the threaded end of the universal handle into the template, place the template over the tissue to be harvested, and then, with scissors or the like, cut around the outline of the template to provide a rough tissue rectangle. Alternatively, the surgeon may simply place four small sutures into the tissue at the corners of the template, remove the template, and then cut out the tissue rectangle. At present, the template is preferably 4 in. by 2 in. in area, and is made from a clear bio-compatible plastic such as polysulfone.

Figure 7B:
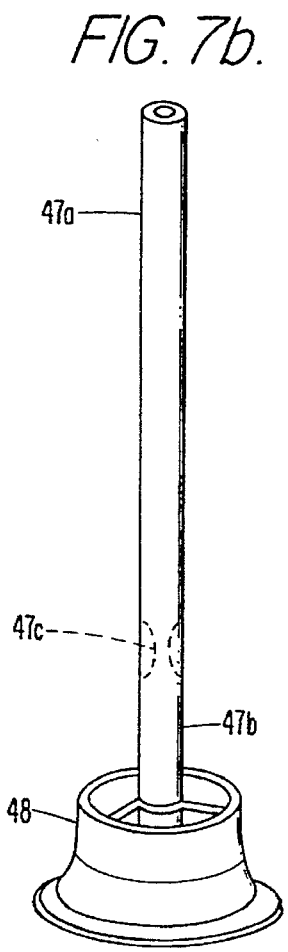
Figure 7F:
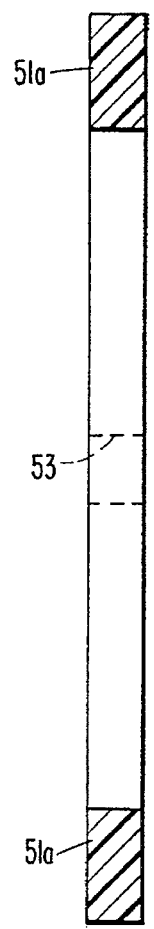

Additional detail on the rough sizing template is provided in FIGS. 7e-7f, in which like elements are referred to with like reference numerals. FIG. 7e provides a top view of the template, which is approximately 4 by 2 inches in area, and is configured with hollow areas 52a and 52b, and solid frame 51a, with central member 51b extending from the top of the frame to the bottom, separating the two hollow areas. A threaded hole 53 is also provided to connect with the universal handle. A side view of the template is provided in FIG. 7f.

It should be appreciated that alternatives to the above-described template are possible for use in harvesting the tissue. A soft and flexible template, for example, could be utilized. This template could be adhered to the tissue temporarily while the tissue rectangle is cut out. Modified forceps are also possible which can be used to guide the surgeon's scalpel. Optical or lighted guides are also possible, which project an image of the template onto the surface of the tissue to be cut, for use in guiding the surgeon's scalpel.

Turning back to FIG. 7a, a tray is also provided, preferably configured to provide basins 25, 26, and 27. These basins are approximately 2 inches deep. Two will preferably be filled with saline or the like, and the third, with saline or optionally a fixative solution. The peripheral basins, 25, 27, are approximately 4 in. by 6 in. One of these basins is configured for use as a rinse basin, and the other is also configured for use either as a rinse basin, and alternatively as a chemical treatment basin. The central basin 26 is approximately 6 inches square, and is configured for use as the central assembly basin. The volume capacity of the two peripheral basins is preferably 500 cc, and for the central basin, 750 cc. These basins will be used as staging and preparation areas in the course of assembling the valve. Basin 25 will advantageously be used to clean the tissue, basin 26, for valve assembly, and basin 27, for tissue rinsing or fixing.

Optionally, a separate third kit could be provided with a tray configured with a basin containing a fixative solution. This kit would be used only for quick fixing the tissue. In this instance, the third basin 27 in the kit of FIG. 7a would be filled with saline, and used as a rinsing basin, and the separate kit would be used for quick-fixing the tissue.

Turning back to the method of valve assembly, after the rough tissue rectangle has been harvested, basin 25 is utilized to clean the tissue and remove any fatty deposits or the like. Once the tissue has been cleaned, it is inspected to ensure that it will be suitable for use in the valve.

At this point, the tissue may optionally be "quick-fixed" by dipping it temporarily in glutaraldehyde or the like. If the surgeon chooses this option, basin 27, the secondary tissue preparation area, is utilized for this purpose. Instead of being filled with saline, however, this basin would be filled with a chemical solution with a low concentration of glutaraldehyde or the like. The tissue is then simply dipped in this solution for about 45 minutes or less, preferably about 10 minutes or less, and most preferably about 5 minutes or less. Alternatively, as discussed earlier, a third kit separate from the other two could optionally be provided for quick-fixing. This kit could have applications in separate surgical procedures such as native valve repair.

This quick-fixing step is desirable since the solution cross links proteins in the tissue to make the tissue stronger and less pliable. This, in turn, makes the tissue easier to handle, and hence more suitable for valve construction. Although the biological effects are not completely known, it also appears that the quick fix is important to the durability and long term survival of the tissue, and may aid in the tissue's transition to a leaflet material. In other words, the ability of the body to nourish and maintain the long-term viability of the tissue may be enhanced by the quick fix.

It should be noted that the function of the glutaraldehyde is different here than for prior art tissue valves utilizing bovine or porcine tissue or the like. With these tissues, glutaraldehyde treatment was important for attenuating the antigenicity of the tissue in a treatment process which typically requires 2–4 weeks, and increasing the inherent strength of the tissue, while here, the tissue is preferably autogenous tissue, which has no significant antigenicity. Therefore, the beneficial aspects of the treatment are different. Here, it appears that the solution selectively kills surface portions of the tissue graft, and that this selective killing may promote long-term viability of the tissue. Also, the time to perform the process is much shorter. As mentioned previously, the autogenous tissue should be dipped into the solution by no more than about 45 minutes, preferably by no more than about 10 minutes, and most preferably by no more than about 5 minutes.

Besides glutaraldehyde, it should be appreciated that other chemical cross-linking agents are possible for use in quick-fixing the tissue, including or in combination, formaldehyde, glycerin, glycerol, or the like.

Turning back to the valve assembly, at this point, the surgeon or assistant is ready to measure the size of the annulus to be fitted. This is where the obturators 22a–22e come into play in conjunction with the universal handle 23.

The surgeon or assistant will simply screw the threaded end of the universal handle into one of the obturators, and then push the obturator into the annulus. The surgeon or assistant will successively perform this step with different obturators from the group 22a–22e until that obturator is determined which will yield the closest fit. Note that in the example, five obturators are provided. It should be appreciated, however, that other examples are possible, including examples where more or less than five obturators are provided.

It should be appreciated also that a variety of sizes of obturators are possible. For replacement of the mitral valve, an atrioventricular valve, it is advantageous to provide a set of obturators with diameters of 31, 29, 27, 25, and 23 mm. It should be appreciated that different sizes, and numbers of obturators may be needed for replacement of aortic/ pulmonary valves. For the aortic valve, it is advantageous to provide a set of obturators with diameters of 19, 21, 23, 25, and 29 mm. For replacement of valves in young children, it is advantageous to provide obturators with smaller diameters, i.e., as small as 14 mm.

It may also be necessary to vary the universal handle depending on the valve type to be replaced. Specifically, the handle is preferably straight for use in sizing the aortic valve, but angled at about 30 degrees for sizing the mitral valve. In either case, whatever angle the handle is initially set at, the handle should be provided with a means to slightly deviate from this angle during use in the operating room.

Figure 7C:
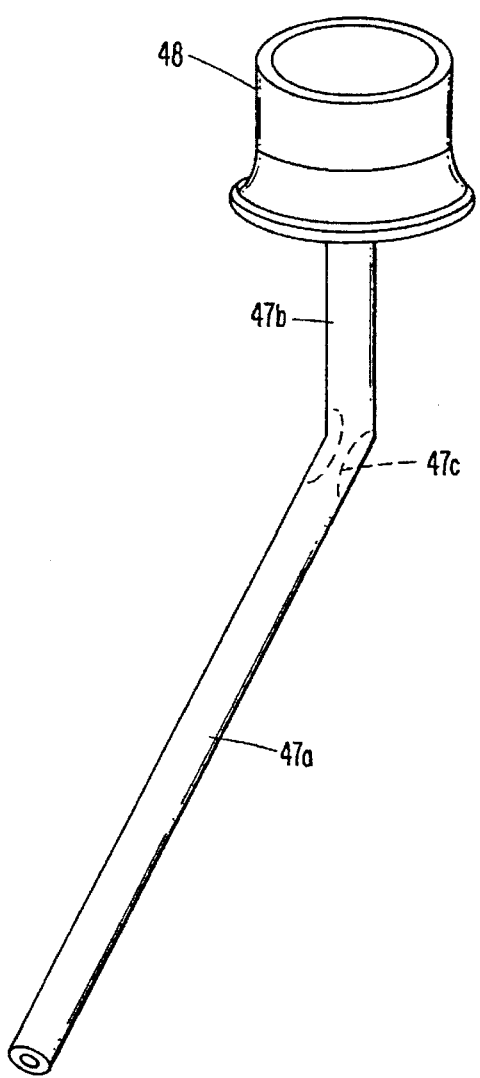

Turning to FIGS. 7b–7c, and FIG. 7g, these figures provide additional detail regarding the universal handle as it is configured for use with the obturators. FIG. 7b illustrates the preferred handle as configured for the aortic valve, while FIG. 7c illustrate the same for the mitral valve.

Turning to FIG. 7b, the preferred handle 47 for the aortic valve is preferably straight, although means, such as malleable section numeral 47c, configured to couple sections 47a and 47b together, should be provided to enable the handle to deviate slightly from this angle. A preferred configuration for obturator 48 is also illustrated. As illustrated, the preferred obturator is configured as a spoked wheel.

Figure 7D:
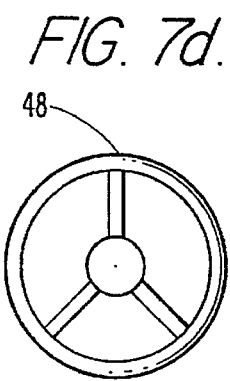

Turning to FIG. 7c, the preferred handle for the mitral valve is illustrated. As indicated, this handle is preferably angled at about 30°, although again, means such as malleable section 47c, used to couple sections 47a and 47b together, should also be provided so that the handle can be deviated from this angle slightly. FIG. 7d illustrates, in greater detail, the preferred configuration for obturator 48.

It is desirable to configure a universal handle that can be used with both valve types. FIG. 7g illustrates such a universal handle. As illustrated, the holder comprises plastic rod 47a connected by malleable wire 47c to shorter plastic rod 47b. The shorter plastic rod is preferably threaded at one end 47d in the manner described previously. The rod 47a is advantageously 6 in. long with a diameter of 0.25 in., while the shorter rod 47b is advantageously 2.0 in. long, with a diameter of 0.25 in. The malleable wire advantageously has a diameter of 0.05 in., and is configured to allow the shorter section 47b to pivot about pivot point 50, by at least about 30 degrees. FIG. 7g illustrates in phantom, the shorter section once pivoted by about 30 degrees in first one direction, which portion is identified with reference numeral 47b(1), and then about 30 degrees in the opposite direction, which portion is identified with reference numeral 47b(2). It should be appreciated that the universal handle of FIG. 7c is preferably configured to be threaded into the obturator from the opposite side than that illustrated in FIG. 7b.

Turning back to valve assembly, at this point, the tissue has been prepared and the annulus sized. The obturators, tissue template, and universal handle are no longer needed, and they may simply be disposed of. Tray 31, however, is kept, since basin 26 is still needed as a construction area for assembly of the valve.

The surgeon or assistant next selects a size-specific aortic or mitral stent kit, which contains all the components needed to complete the assembly of the valve. Again, for the mitral valve, size-specific stent kits configured for five annulus sizes, 23, 25, 27, 29, and 31 mm, are desirable, while for the aortic kit, 19, 21, 23, 25, 27, and 29 mm kits are desirable. It should be appreciated that other size kits are possible, i.e., a 14 mm kit for young children.

Figure 8A:
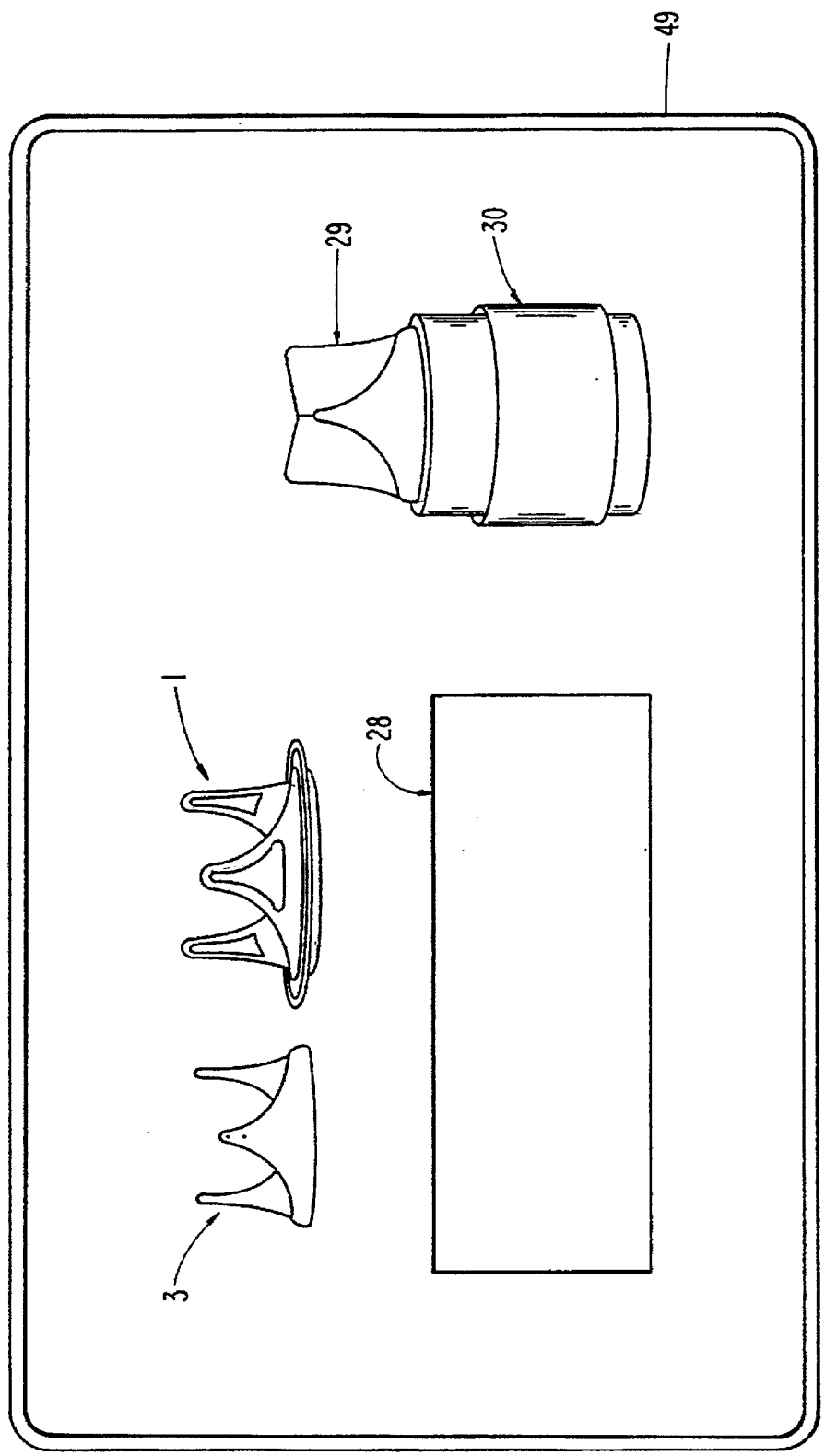

The components in the size specific stent kit are illustrated in FIG. 8a, in which, compared to earlier figures, like elements are referred to with like reference numerals. As indicated, this kit contains tray 49 configured to hold inner stent 3 (already covered by and thermal-bonded to its corresponding DACRON cover), outer stent 1 (already integrated with a garter spring and elastomeric ring and also covered and thermal-bonded to its corresponding DACRON cover), size-specific tissue cutting tools 28, assembly mandrel 29, outer stent spreading tools 30, adapters for mounting the valve in a valve tester (not shown), and optionally a valve holder (not shown) for use by the surgeon to hold the valve during implantation.

Turning back to valve assembly, after selecting the appropriate stent kit, the surgeon or assistant next further cuts the tissue rectangle to obtain the exact geometry required for valve construction. To accomplish this, the surgeon or assistant utilizes tissue cutting tools 28.

Figure 8C:
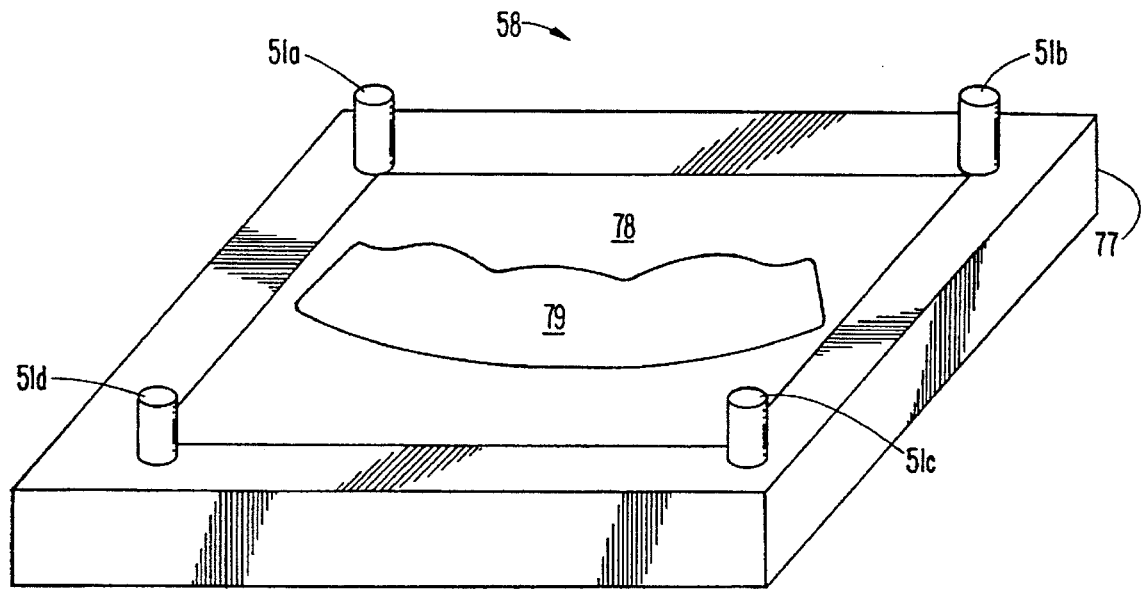

At present, these tools comprise tissue cutting die 31, and base 58. An embodiment of the tissue cutting die is illustrated in FIGS. 8d-8f; a second embodiment is illustrated in FIGS. 8g-8i. The base 58 is generally illustrated in FIG. 8c, and with more detail, in FIGS. 8j-8k.

Turning to the die first, this die comprises a razor-sharpened and honed blade 33 embedded in thermoplastic frame 54. Also included are a plurality of ferrule pairs 34a, 34b, 34c, and 34d, which are also embedded in the thermoplastic.

Figure 8B:
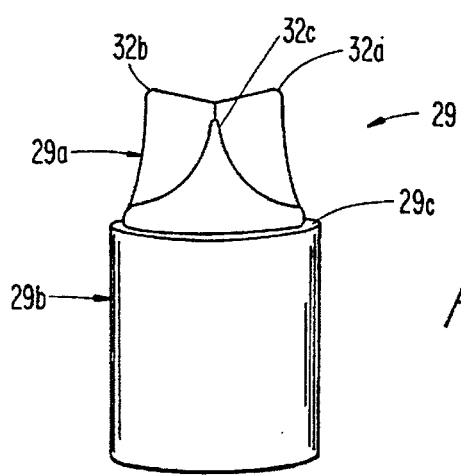
Figure 8F:
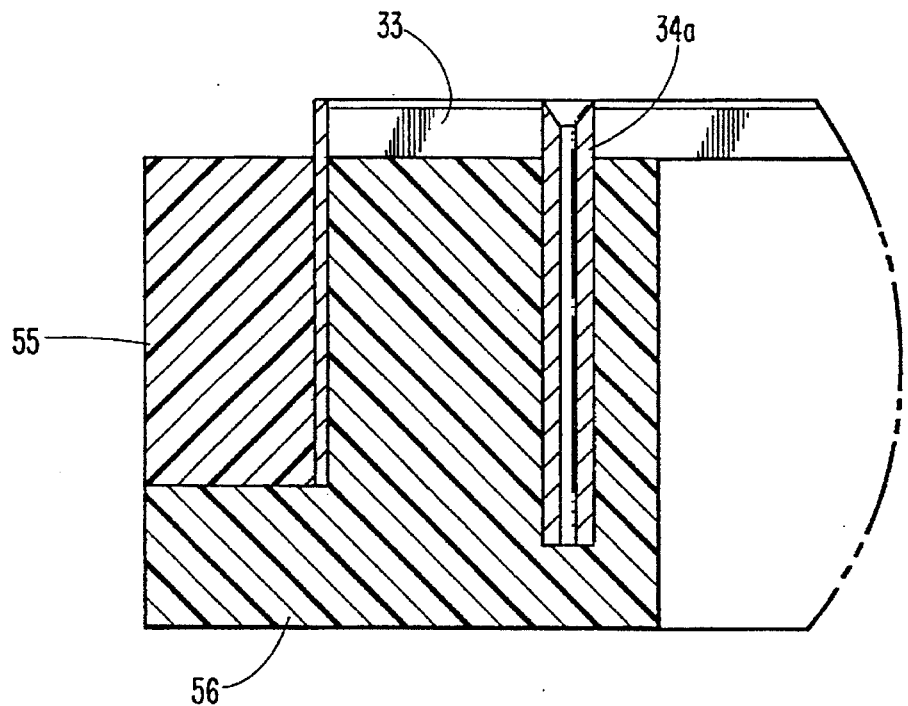
Figure 8I:
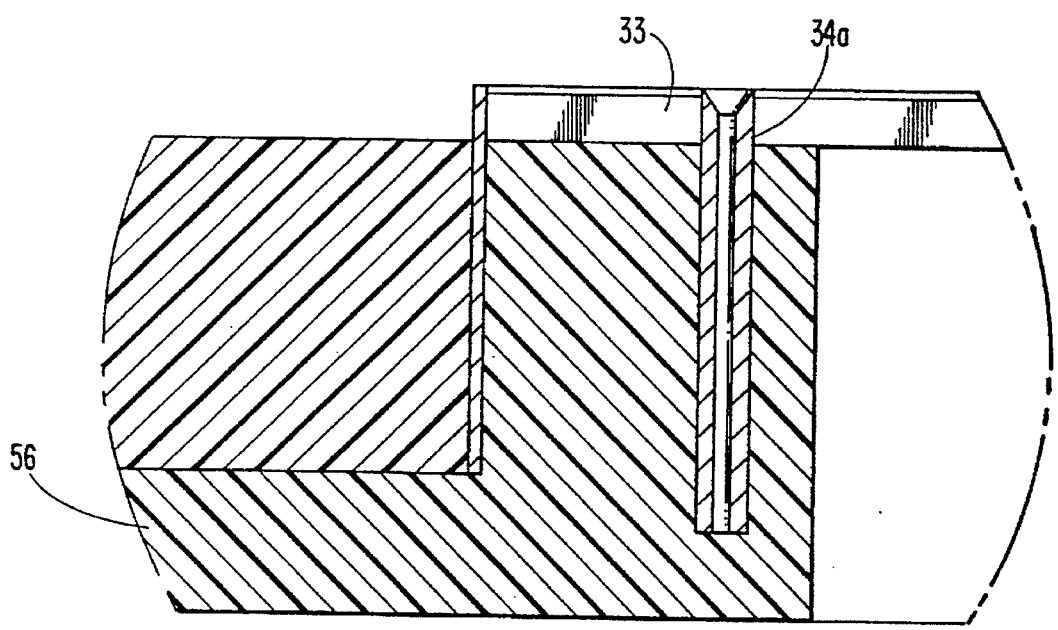
Figure 8G:
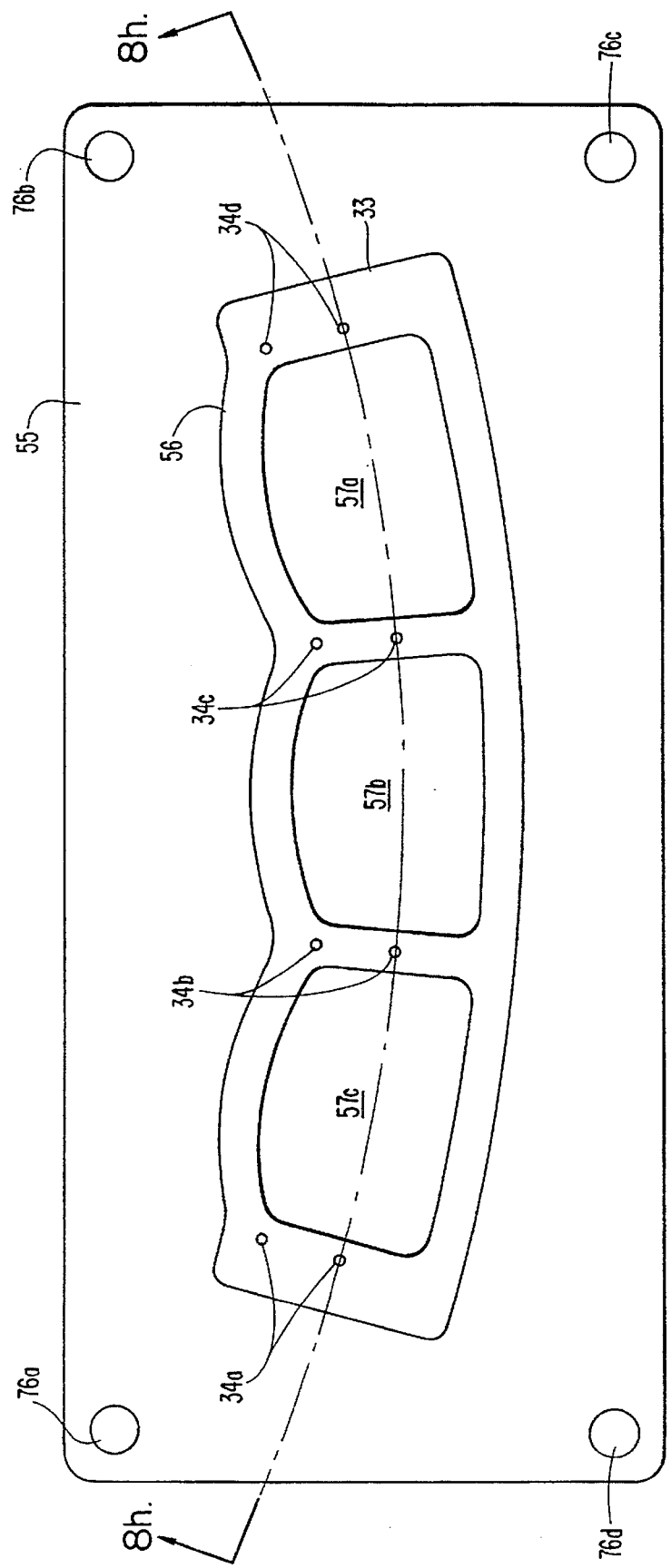
Figure 8K:
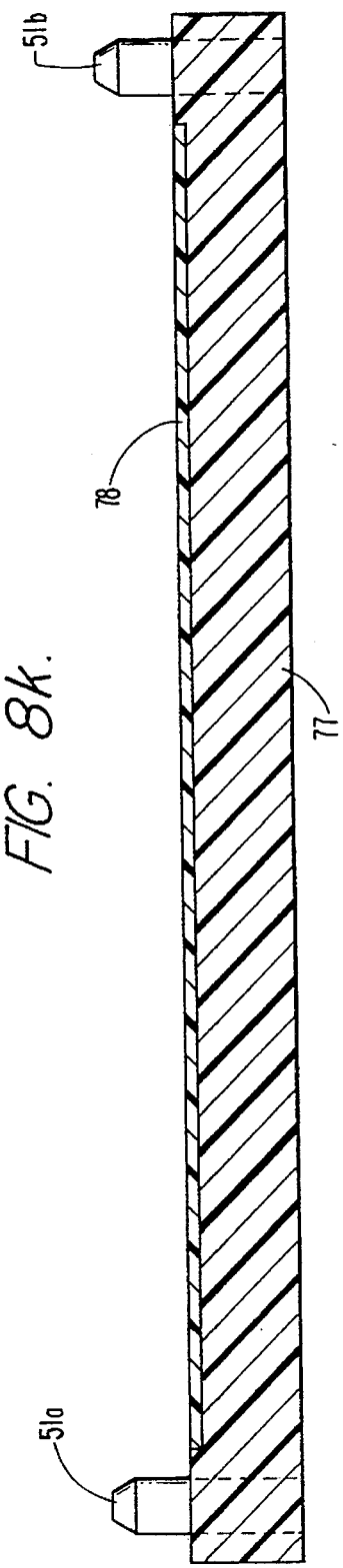
Figure 8L:
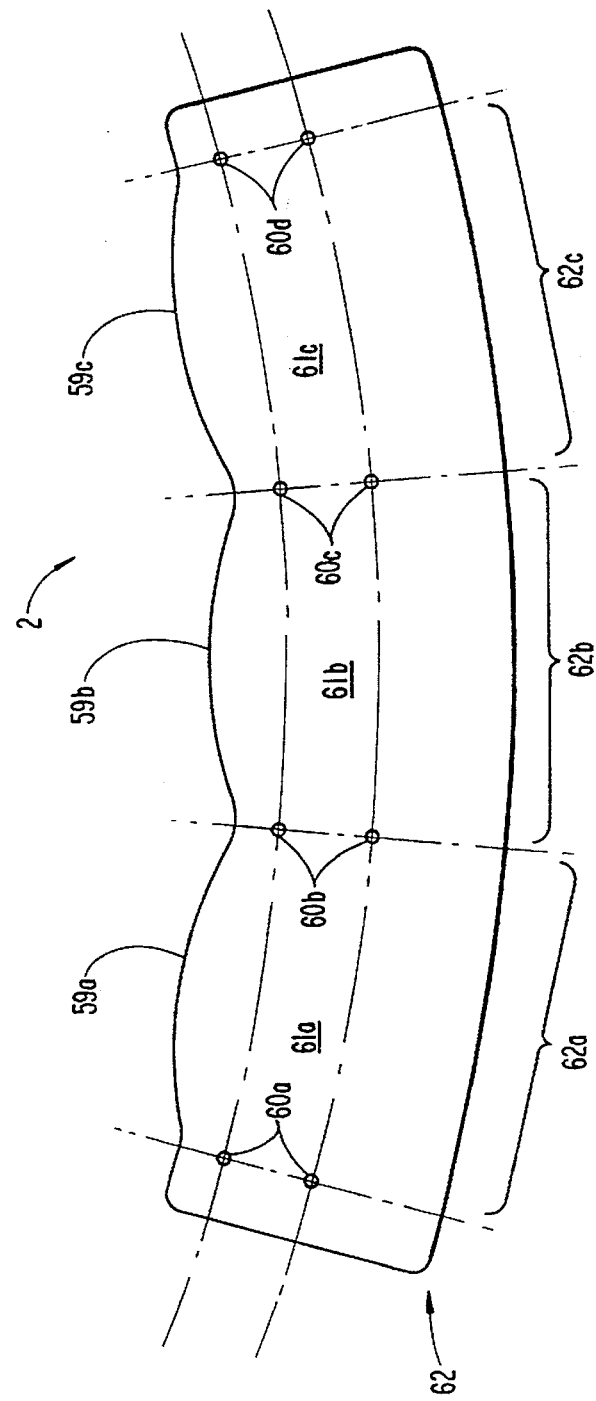
FIG. 8l illustrates the tissue cut into a specific configuration for insertion into the valve.

The objective of this step is to process the roughly-sized tissue rectangle into the specific geometry, illustrated in FIG. 8l, needed for construction of the valve. To perform this step, the surgeon or assistant simply places the rough tissue triangle on the base 58, locates the die over the tissue, and presses down on the die in a similar manner to a cookie cutter to cut out the corresponding tissue 2.

The blade 33 is typically sharpened to about 100–300 Angstroms (by contrast, a surgeon's scalpel is typically only sharpened to about 300 Angstroms), and preferably, to about 150–200 Angstroms, and extends about 35 mils above the upper surface of the thermoplastic frame 54. Therefore, only a small amount of pressure on the die will be required to cut out the tissue. Other methods or tools, i.e., a screw or hand-held clamp, which predetermine and limit the cutting force and depth, may be used to cut the tissue.

The blade is preferably shaped to have the same outline as the desired tissue 2 illustrated in FIG. 8l. In addition, the ferrule pairs 34a–34d are preferably positioned and sized to cut appropriately positioned holes in the tissue 2, which will ultimately be registered with the tissue alignment members extending from the inner stent. At present, the ferrules are advantageously approximately 0.025 in. in diameter, and the blade is constructed from Sandvik 6C27 or equivalent and the ferrules are constructed out of 316 or 303 stainless steel, but it should be appreciated that other materials are possible, including thermoplastics, composites, ceramics, or combinations of the above.

In FIG. 8d, four pairs of ferrules are shown in the tissue cutting die. FIG. 8l shows the resulting holes which are cut into the tissue. It should be appreciated, however, that other hole configurations are possible. The purpose of the holes is to enable the tissue to be precisely positioned with respect to the inner stent during valve assembly, and prevent circumferential movement of the tissue, or movement of the tissue up or down, during the valve assembly process. As mentioned previously, improper placement, or circumferential or other movement of the tissue during the valve assembly process can lead to prolapse, which can induce undue strain on the valve, and leakage of the valve. Specifically, with respect to FIG. 8l, if section 59a of the tissue were to be stretched too tightly during the valve assembly process, the co-aptive edge of the leaflet formed by this section may not properly join with the co-aptive edges of the other two leaflets, but will instead, strike these leaflets below their co-aptive edges. The result is that the co-aptive edges of the leaflets formed by sections 59b and 59c will not be able to transmit stress to the co-aptive edge of leaflet 59a, with the result that leaflets 59b and 59c will be subjected to undue stress. Moreover, leaflet 59a will be subjected to undue stress as well. This is because leakage may be induced at the center of the valve, and this leakage will exert strain on leaflet 59a while the valve is in a closed position. The registry of the holes with the tissue alignment member helps prevent prolapse, and therefore eliminate this stress and leakage problem.

Therefore, other configurations of holes and corresponding tissue alignment members are possible, as long as the above objective is achieved, including configurations where more than two members are configured on each stent post, or where members are also distributed around the annular base of the stent. However, in all these configurations, the number of holes and corresponding members should not be too great since too large a number of holes may unacceptably slow down the assembly process as the surgeon or assistant attempts to register all the holes with the corresponding tissue alignment members. By contrast, the valve described in the '483 patent employs a total of 27 pins and studs, which must be registered with corresponding holes or slots in the outer stent. This configuration makes it difficult or impossible to assemble this valve in the limited time available in the operating room.

Moreover, the number of members should not be too large so as to create mechanical fixation points in the assembled valve. If too large a number of members is utilized, the numbers may begin to play such a role in the assembled valve. Specifically, the tissue alignment members are designed to only position the tissue during valve assembly, and their primary role ceases after valve assembly. This is because in the assembled valve, as stated previously, the clamping force generated by the stents substantially holds the tissue in place to more uniformly distribute stress. If the tissue were to be held in place in any significant degree by the members after assembly, then the stress would be focused at these mechanical fixation points, which could lead to premature tearing of the valve.

Finally, in all configurations, the members should not be configured to connect to the outer stent, or to project into corresponding holes in the outer stent which register with the members. This is why the outer stent is not configured to have any holes which register with the members. If the members connected to or registered somehow with the outer stent, then the members could begin to play a fixation role in the completed valve, and further, mechanical fixation of the two stents could impede the flexible nature of the stents.

As discussed previously, the stents of the subject invention preferably have flexible frames made of thermoplastic. The flexible nature of the stents further contributes to the ability of the assembled valve to withstand stress. If pins or studs were used to connect one stent to another, then for one stent to flex, it would have to pull the other stent along with it. Consequently, the flexing of the stents would be impeded, which would form even more stress on the tissue and pins.

A preferred configuration is about nine members or less distributed around the inner stent. Preferably, the members do not extend into holes or slots in the outer stent. It should be appreciated, however, for the reasons stated earlier, that other configurations are possible.

Turning to FIGS. 8d–8f, the die is configured with two plastic blocks, identified with numerals 55 and 56. These blocks are preferably constructed from a clear or translucent plastic, biomedical grade material. The ferrules are embedded in block 56. Block 55, in turn, is embedded within block 56. Blade 33 is embedded at the interface between the two blocks. Block 56 is also configured with hollow regions 57a, 57b, and 57c, within it, to provide enhanced visibility of the tissue being cut. A side view of the die of FIG. 8d is provided in FIG. 8e, while FIG. 8f provides additional detail on the blade and ferrules. In this embodiment, the blade is preferably razor-sharpened to about 150–200 Angstrom, extends 35 mils above the blocks, and is parallel to the surface of the block within a tolerance of 1 mil. The ferrules also preferably extend 35 mils above the blocks, and are parallel with respect to the surface of the blade within a tolerance of 1 mil.

Turning, for the moment, to the base to be used in conjunction with the die, as illustrated in FIG. 8c, the base actually comprises several components, including block 77, cutting pad 78, outline 79, and guide pins 51a–51d.

The block 77 is preferably made of a material that is clear or translucent, so that, if desired, it could be back-lit. Moreover, the material should be such that the base may be disposed of or recycled.

The cutting pad 78 is preferably a thin, i.e., 0.025 inch or less, sheet of TEFLON or the like, and is configured to provide an appropriate amount of resiliency against the razor sharp blade of the die. The thickness of the pad is determined by the extent to which blade 33 extends above the upper surface of the cutting die 36 and by the thickness of the tissue used. In the example discussed earlier, the blade extension is 35 mils, and human pericardial tissue may be about 10 mils thick. The thickness of the pad should be the difference, i.e., 25 mils, in this example. The cutting pad functions to limit the blade penetration into the tissue and the base on which it is resting.

The cut outline 79 is an outline of the desired tissue piece, and can either be integrated into the cutting base or cutting pad. This outline is used to project an outline of the cut pattern through the transcalent tissue so that the valve builder can precisely know which portion of the tissue will be cut, and can thereby avoid any undesirable portions of the tissue, including irregularities, adhesions, or areas which may contain too much or too little collagen.

The guide pins 51a–51d index with holes in the cutting die.

In cooperation with the cutting die 31, the cutting base can be used as follows. First, placed over the rectangle would be placed over the cutting pad until the desired portion of the rectangle is over the outline on the cutting pad. Then, optionally in cooperation with the guide pins, the cutting die is lowered until the blade in the die cuts the tissue exactly as in the outline.

FIGS. 8j–8k provide additional detail on the cutting base 58. Compared with FIG. 8e, like elements are referenced with like identifying numerals in these figures. FIG. 8j is a top view of the base, while FIG. 8k is a side view. The block 77 in this example is dimensioned to be 3.5 in. by 1.5 in. by 0.25 in. Moreover, the guide pins in this example are configured to have a diameter of about 0.125 in., and to have tapered ends as shown.

An alternative embodiment of the tissue cutting die 58 is illustrated in FIGS. 8g–8i, in which, compared to FIGS. 8d–8f, like elements are referenced with like identifying numerals. An important aspect of this embodiment is that it is configured to cooperatively interact with the cutting base of FIGS. 8j–8k.

In this embodiment, the blade 33, and block 56 are embedded in a second block 55 configured to have about the same shape as the block 77 of the cutting base 58. Block 55 is also configured with indexing holes 76a–76d, which are adapted to mate with the indexing pins 51a–51d of the cutting base 58. In the particular example illustrated, the holes are configured with a diameter of 0.125 in. With this embodiment, the rough tissue is cut by placing it on the cutting pad of the base, and then lowering the die to cut the tissue with the pins of the base indexing with the corresponding holes in the block 55 of the die.

The preferred tissue pattern of the precisely cut tissue is illustrated in FIG. 8l. As illustrated, the tissue pattern is a flat conical geometry, that is, it is a cone unwrapped onto a flat surface, with leaflet edges 59a, 59b, and 59c formed from a plurality of radii extending from a free margin.

An important aspect of the pattern is the placement of hole pairs 60a, 60b, 60c, and 60d, which are cut into the tissue by ferrules 34a, 34b, 34c, and 34d of the tissue cutting die. These holes are small, having a diameter of about 25 mils, so that they will register with the tissue alignment members, 6a and 6b, extending from the inner stent. Although the body of the members should have a diameter of 25 mils, the heads of these members should have a diameter slightly greater than 25 mils, since they are formed by flattening the tips of members 6a, 6b, illustrated in FIG. 2d, which are initially formed with a 25 mil diameter. Consequently, when the precisely cut tissue is wrapped around and registered with the inner stent during valve assembly, these holes will literally be "popped" over the tissue alignment members, and thereafter be prevented from circular, or up or down, movement by the members. Moreover, these holes are precisely placed so that the tissue used to form each of the leaflets in the assembled valve, identified with numerals 61a, 61b, and 61c in FIG. 8l, respectively, will be uniform. Consequently, the hole pairs should be uniformly radially spaced so that the resulting leaflets will be uniformly sized. Also, in FIG. 8l, each of the resulting bottom edges of each leaflet, identified with numerals 62a, 62b, and 62c, should extend radially uniformly.

Variants on the tissue cutting tools are possible. Specifically, the block could be configured from a range of materials besides thermoplastic, such as TEFLON. In addition, the blocks 55–56 could be constructed out of a number of materials, including polycarbonate, polysulfon, nylon, epoxy, or the like, as long as the material is biocompatible. It is desirable for the blocks to be translucent. This latter requirement is so that the surgeon or assistant can more precisely align the tissue die over a particular portion of the rough tissue rectangle that the surgeon or assistant believes is more desirable than others for use in the assembled valve.

Alternatively, instead of using a die, a soft template made of silicone or the like could be temporarily adhered to the tissue, and then the tissue cut out by following a scalpel along the outline. Alternatively, the tissue could be marked with an FDA-approved dye while the template is in place, the template would then be removed, and the tissue cut out using the pattern formed by the dye on the tissue. Other possibilities include laser based or water jet systems with or without computer assistance, male/female dies, modified forceps to be used with conventional surgical cutting instruments, and optically generated templates projected onto the tissue. Hand held devices, such as modified forceps or the like, adapted to close a base and corresponding die together to cut the tissue using hand pressure, are possible.

Variants of the tissue configuration to be formed are possible also. Specifically, instead of being configured as the precisely cut pattern illustrated in FIG. 8l, the tissue could be configured as three separate precisely cut pieces, corresponding to the three valve leaflets, which pieces could then be separately arranged around the inner stent. A possible problem with this approach may be that it could adversely affect the clamping ability of the stents. This is because these three sections will need to overlap slightly at the posts of the inner stent, leading to three seams having twice the thickness of the tissue itself. These seams may interfere with or prevent the clamping of the tissue between the seams. Hence, the single piece configuration is preferred.

In the subject valve, the self-adjusting tensioning means provides the capability of adjusting for tissue irregularities, and hence, could overcome this problem. The valve described in the '483 patent, on the other hand, utilizes pins and studs to hold the tissue in place in the assembled valve. This approach, however, is very time-consuming to assemble, and leads to undue stress buildup. Hence, the use of the self-adjusting tensioning means is preferred.

Turning back to the valve assembly process, the next step is to position the inner stent utilizing assembly mandrel 29. The basin 26 in the preparation and sizing kit illustrated in FIG. 7a provides a convenient construction area for placement of the mandrel.

Turning to FIG. 8b, this figure illustrates the mandrel in more detail. As illustrated, the assembly mandrel comprises two sections, a base 29b and a top portion 29a, with an edge 29c along the periphery of the base at the junction with the top portion. Preferably, the top portion 29a is a replica of the leaflets of the desired valve when placed in a closed position.

After the mandrel has been positioned, the next step is to place the inner stent over the top of the mandrel until the bottom of the stent rests against the edge 29c. In the course of placing the inner stent over the mandrel, the posts of the inner stent are placed over corresponding sections 32a, 32b, and 32c within the top portion, 29a, of the assembly mandrel. The inner stent is also advantageously indexed to the mandrel, through the use of appropriately configured detents or the like, in order to facilitate placement of the inner stent over the mandrel.

After the inner stent has been positioned on the mandrel, the cut tissue 2 is applied to the inner stent by popping, in succession, the paired holes in the tissue with the corresponding tissue alignment members extending from the inner stent posts, and placing the bottom edge 62 of the tissue in proximity to the bottom of the annular base of the inner stent. The result is to wrap the tissue around the stent to form a tissue configuration in the shape of a cone. The ends of the tissue in the proximity of the first and last pairs of holes, identified with numerals 60a and 60d in FIG. 8l, will be popped over the same tissue alignment members, causing this tissue to overlap slightly, and eliminating the need to suture the ends of the tissue together. Although a small seam of double thickness will be formed, this one seam has been found not to interfere with the clamping effect of the stents.

Turning back to valve assembly, once the tissue has been mounted over the inner stent, it is then smoothed over the mandrel. This smoothing step acts to configure the tissue into the three valve leaflets, and to further position the leaflets into a closed resting position. Each leaflet is smoothed over the mandrel to eliminate wrinkles, puckers, or other irregularities in the tissue that could preclude a successful valve assembly.

At this point, the outer stent spreading tools 30 come into play. These tools are illustrated in FIGS. 9a–9d, in which like elements are referred to with like identifying numerals. The outer stent spreading tools 30 comprise sleeve 80, top spreading tool 35, and spreading bullet 36. All these components are size-specific, and hence provided in the stent kit. The objective of these components is to spread open the outer stent, enabling it to be easily situated over and placed in a close mating position with the inner stent with the tissue clamped in place without damaging the tissue.

Figure 9A:
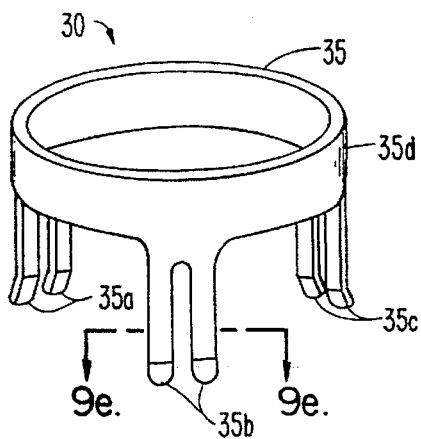
FIGS. 9a–9e illustrate the components of outer stent spreading tool.
Figure 9E:
Figure 9B:
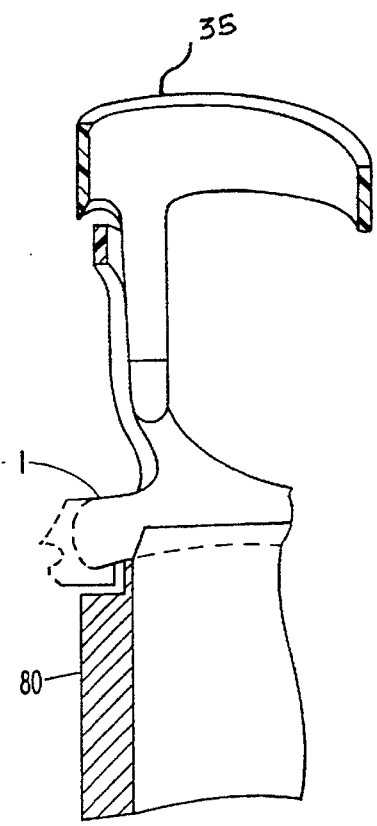
Figure 9C:
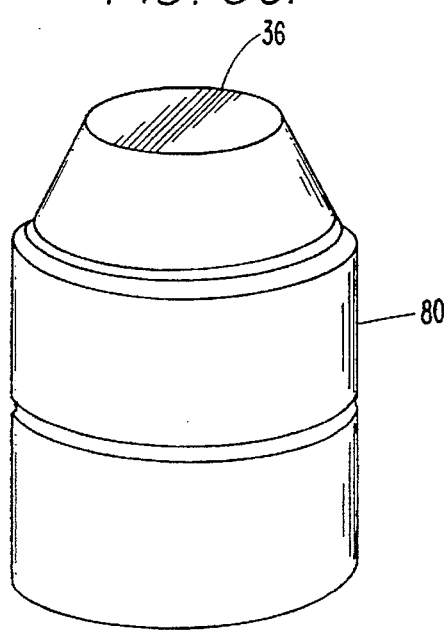
Figure 9D:
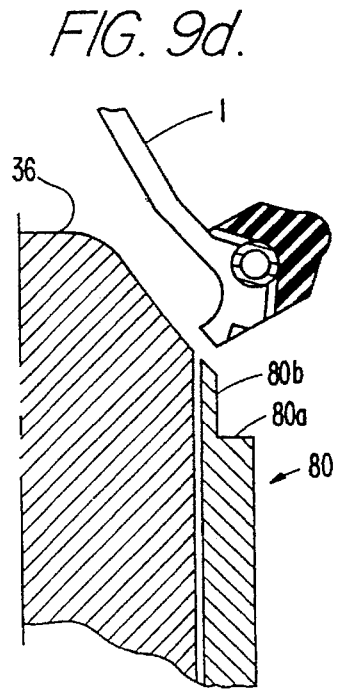

To accomplish this objective, first, sleeve 80 is placed over the spreading bullet 36, as illustrated in FIG. 9c. As illustrated in FIG. 9d, which is a cross-sectional view of the sleeve 80 while situated on the bullet 36, the sleeve 80 has a tapered cuff portion 80b, which facilitates sliding the outer stent over the sleeve. As mentioned previously, the outer stent is configured with window extensions, slots, or the like, along the annular base, enabling the stent to be splayed open. The outer stent is pushed, bottom first, over the top of the spreading bullet. The bullet causes the outer stent to spread open, and the tapered cuff promotes the sliding of the annular base of the outer stent onto the sleeve 80 until the bottom of the annular base of the stent is resting against ledge 80c of the sleeve.

Next, the spreading tool top 35 comes into play. This top is illustrated in FIG. 9a. As illustrated, the top comprises three blade pairs, 35a, 35b, and 35c which pairs extend from, and are about equally spaced around the periphery of an annular cusp 35d. The objective of the top is to sustainably spread the posts of the outer stent outward. The blade pairs are configured such that the two blades making up one of the pairs are capable of coinciding with the left most and right most struts making up the corresponding post in the outer stent.

Turning to FIG. 9b, the top 35 is then fitted onto the outer stent, the bottom of which is already sustainably splayed upon by the sleeve 80, so that each pair of blades is aligned with the stents in the corresponding outer stent posts. This causes the posts of the outer stent to spread open.

Next, sleeve 80, assembled in conjunction with the top 35 to hold the outer stent open, is removed from the spreading bullet. This assembly is then placed over the assembly mandril, and then lowered until the outer stent is in position to mate with the inner stent, i.e., the posts are aligned, etc. The action of the sleeve and spreading tool top, in sustainably opening the outer stent, ensures there is no contact between the outer stent and the tissue which could result in damage to the tissue. When the outer stent has been appropriately positioned, the sleeve 80 is pulled downwards, causing it to separate from the outer stent, which is restricted from moving downwards also by the inner stent. With the removal of the sleeve, the annular base of the outer stent, through the action of the self-adjusting tensioning means, collapses over the annular base of the inner stent, to clamp that tissue situated along the annular base of the inner stent.

The outer stent spreading tool sleeve 30c and the inner stent and both preferably indexed to the mandrel through a plurality of cooperating detentes in the mandrel to aid in alignment of the outer stent over the inner stent. Alternatively, the sleeve and inner stent could be indexed through a pin and slot arrangement.

Next, the spreading tool top 35 is pulled off the top of the outer stent, causing it to separate from the outer stent, which is restricted from moving upwards also by the locking flange 12, which by this time, will be in locked position under the base of the inner stent. This action releases the posts of the outer stent, and allows them to retract to mate with the corresponding posts of the inner stent, and securely clamp the tissue situated behind the posts of the inner stent, and along the scalloped edge connecting the posts of the inner stent.

After this step is performed, the valve assembly is completed, and the final step, valve testing, can begin.

As stated previously, a significant aspect of the completed assembly is the enhanced clamping of the tissue provided by the stents, and the elimination of mechanical fixation points between the tissue and the stents. Not only will the tissue which is situated along the annular bases of the stents be clamped securely in place by this arrangement, but the tissue situated at the posts and along the scalloped edge between the posts will also be clamped securely in place. Because of this enhanced clamping, and elimination of mechanical fixation points, stress will be more uniformly distributed throughout the valve. The long term durability of the valves is therefore improved.

The clamping along the annular base is provided by the garter spring, while the clamping at the posts and scalloped edge is provided by the nesting of the inner and outer stent posts. Note that after the stents have been covered with DACRON fabric and after the tissue has been placed over the inner stent, complete nesting of the stent posts can no longer occur. However, the tapering of the outer stent posts towards the inner stent still ensures that a sufficient clamping force will be generated to hold the tissue in place.

Another significant aspect of the completed assembly is the cessation of the primary role of the tissue alignment members after valve assembly. As indicated previously, the primary role of these members is to ensure proper placement of the tissue, and to prevent movement of the tissue during valve assembly, thereby reducing or eliminating prolapse. In the completed assembly, though, it is important that these members not form mechanical fixation points of the tissue to the stents, since stress would then be concentrated at these points, possibly leading to premature tearing of the tissue at these points, and hence, failure of the valve. This objective is accomplished through the enhanced and self-adjusting clamping, which is sufficient to hold the tissue in place.

Figure 10A:
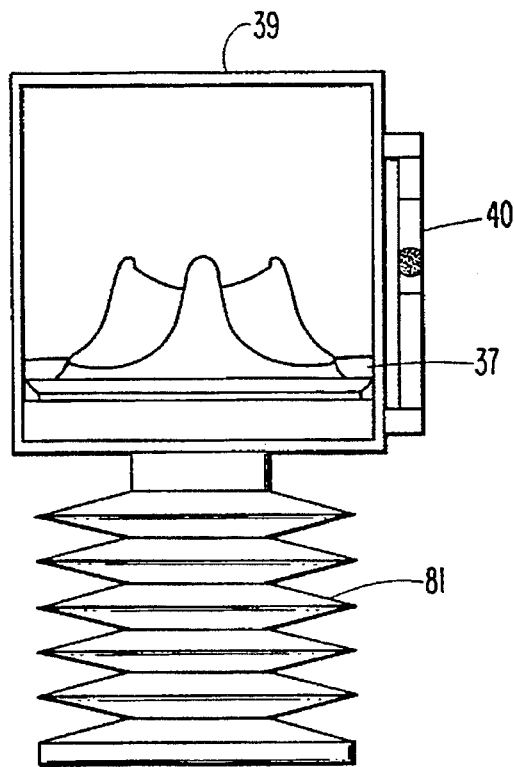
FIGS. 10a–10c illustrate embodiments of the valve tester.
Figure 10B:
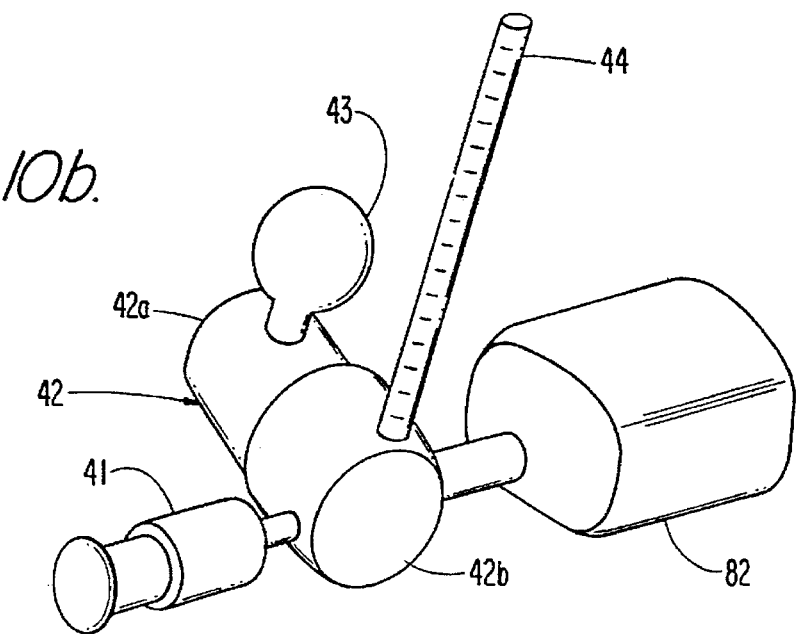
Figure 10C:
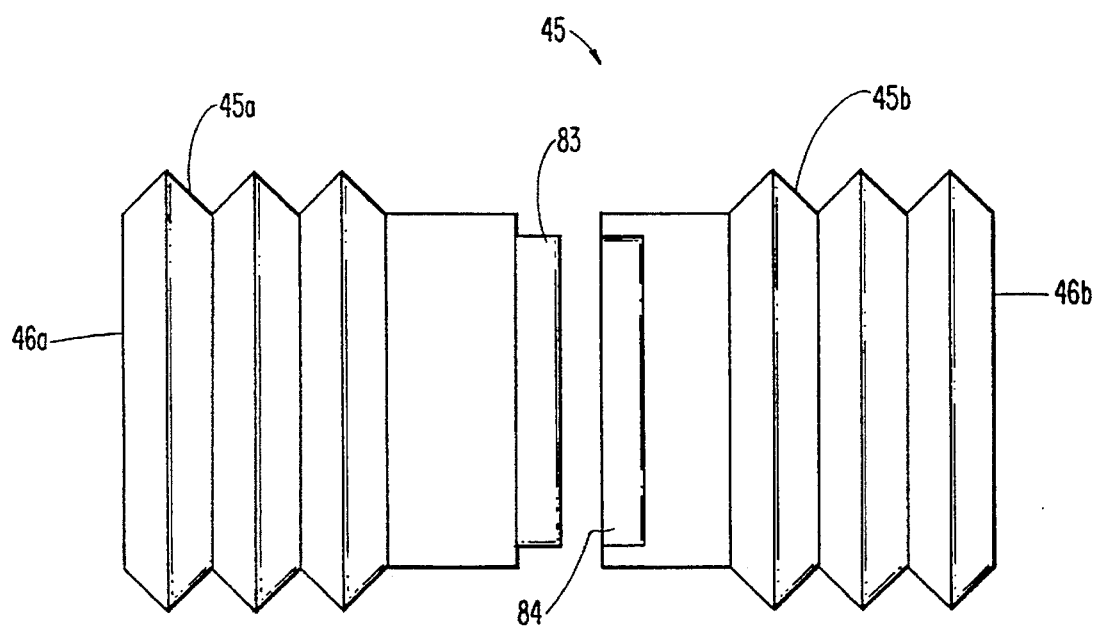

Turning now to the testing device, two possible embodiments of the testing device are illustrated in FIGS. 10a–10c. The purpose of the testing device is to rapidly test the valve before implantation to ensure it is not leaking unacceptably and does not have any other significant flaws.

Turning to FIG. 10a, the tester comprises bellows 81, valve adapters 37, calibrated float 40, and clear viewing chamber 39. The bellows are preferably calibrated, having a known volume and spring rate. The adapters 37 are used to mount the valve in the tester while preventing leakage around the sewing base. These adapters are size-specific to the particular valve to be tested, and hence are preferably provided in the size specific stent kit. The tester itself could, as well, be provided in the kit, or alternatively, could already be available in the operating room. The clear viewing chamber 39 enables the valve during the observe the valve during testing. The calibrated float 40 provides a means to functionally measure leakage or pressure differential across the valve.

This tester operates as follows: First, the bellows is used to displace a known volume of saline through the valve. After this is accomplished, the spring rate of the bellows applies a known back pressure to the closed valve. The calibrated float is calibrated to be in a "safe" zone if there is little or no leakage through the valve. If there is significant leakage, the pressure differential across the valve will change over time, causing the float to move out of the safe zone.

Turning to FIG. 10b, this figure illustrates a different embodiment of the tester. In this embodiment, the tester comprises reservoir 82, syringe 41, testing body 42 with viewing ports 42a and 42b, balloon 43, and manometer 44. The reservoir, syringe, balloon, and manometer are all coupled to the testing body. In addition, the syringe, balloon, manometer, and reservoir all have openings to the tester body which can be selectively opened or closed.

In this embodiment, to test a valve, the valve is preferably mounted in the tester body between the balloon and the manometer, such that it opens in the direction of the balloon. Next, the reservoir is filled with saline. After the valve has been mounted, the syringe 41 is pulled back while only the opening to the reservoir is open, and while the openings to the balloon and manometer are kept closed. This causes the syringe to fill up with a known volume of saline, for example 60 cc. Next, the opening to the reservoir is closed, the opening to the manometer is continued closed, and the opening to the balloon is opened. Then, the saline in the syringe is ejected, causing the saline to flow through the valve and into the balloon, causing it to expand. At this point, just before the balloon recoils, the syringe opening is closed, the reservoir opening is continued closed, and the manometer opening is opened. Since the balloon is preferably calibrated, after receiving the known volume of saline, e.g., 60 cc, from the syringe, and expanding, the balloon will exert a known pressure, e.g., 120 mm Hg, on the valve.

Next, as the balloon exerts pressure on the valve, any leakage of the saline through the valve will then enter the manometer. In the example of FIG. 10b, the manometer is about 12 cm. long, and is calibrated so that each 1 cm. equals about 1 cc of leakage. The manometer thus provides a direct means of measuring the leakage of the valve.

After the manometer is read, it is drained back into the reservoir while the opening to the reservoir is opened, and the remaining openings are continued closed. Alternatively, it is drained while the syringe (and possibly reservoir) is opened, and the syringe is retracted, causing the saline to flow into the syringe. It should be appreciated that in this embodiment, other means besides a syringe, such as bellows or the like, are possible for injecting saline through the valve.

A third embodiment of a tester is illustrated in FIG. 10c. As illustrated, this embodiment comprises a double bellows arrangement 45, with the two bellows in the arrangement identified with reference numerals 45a and 45b. These two bellows are both calibrated and are capable of displaying a known volume of saline, and generating a known back pressure on the valve. A valve mount 83 is provided, and is placed on one of the bellows, bellows 45a in the example, which in turn is calibrated to couple with the mount. Also, means 84 is provided to enable the two bellows to be mated to each other at the valve mount. Further, the outer ends of the two bellows, 46a and 46b, respectively, are clear, enabling a viewer to view the testing process.

In this embodiment, the valve is first mounted on the valve mount 83, and the mount is further positioned within the bellows 45a. Then, one of the bellows is used to displace a known volume of saline through the valve. At this point, a known pressure is exerted on the valve, either by a direct pressure exerted by the other bellows, or a vacuum created by the one bellows. The leakage, if any, of the valve is then visually observed.

Other embodiments of the valve tester are intended to be included, as long as such an embodiment provides the following three capabilities. First, it must be capable of generating a known closing pressure on the valve, either by exerting a direct pressure, or by generating a vacuum. Second, it must contain a manometer, a pressure transducer, or other means for measuring leakage and pressure differential across the valve. Third, it must provide a quick mount system which is adaptable to all valve types.

Variants and additions to the tester are also possible. For example, a magnifying lens could be provided in the viewing ports to provide enhanced visual observation of the valve during testing. Or, a light source could be added to make it easier to observe the valve undergoing testing.

Turning back to valve assembly, assuming the valve is acceptable, the valve is then implanted. At this point, the remaining components in the two kits, and the kits themselves, being dispensable, could be thrown away.

Upon assembly of the valve, the next step is to implant the valve in the annulus. This is accomplished using a holder, with which the surgeon can hold the valve in place while suturing it to the annulus.

While embodiments and applications of this invention have been shown and described, it should be apparent to those skilled in the art that many more modifications are possible without departing from the inventive concepts herein. The invention, therefore, is not to be restricted, except in the spirit of the appended claims.

What is claimed is:

1. A pair of first and second pre-fabricated, sterile kits for use during open heart surgery to provide tools and apparatus for very rapidly manufacturing a prosthetic heart valve immediately following (a) harvesting of tissue from a patient, (b) opening of the patient's chest cavity to expose the patient's heart and (c) excising of a heart valve of the patient's heart needing replacement, thereby leaving an open annulus within the heart, said first kit being a tissue harvesting and annulus sizing kit comprising a tray containing, for rapid availability, the following components for harvesting the tissue and quickly and accurately measuring said open annulus within the patient's heart:

a tissue sizing template formed of a soft and flexible bio-compatible material for positioning directly upon the tissue to be harvested with said template being used as a guide to cut a piece of the patient's tissue in the desired configuration;

a series of obturators of different size which the surgeon can selectively push into said open annulus to ascertain the size of the prosthetic heart valve to be constructed during the open heart procedure;

a first basin for holding a solution for rinsing said tissue;

said second kit being a size specific kit as determined by the annulus measured by using said first kit, said second kit comprising a tray containing, for rapid availability, the following components:

a cutting die for cutting out a portion of said harvested tissue along a perimeter sized to said measured annulus, said cutting die having a substantially continuous blade with a plurality of repeating curved segments, an inner and outer stent sized to said measured annulus, and an assembly mandrel for mounting said tissue between said inner and outer stents for permanently assembling a prosthetic heart valve sized to said measured annulus.

2. A pair of first and second pre-fabricated, sterile kits for use during open heart surgery to provide tools and apparatus for very rapidly manufacturing a prosthetic heart valve immediately following (a) harvesting of tissue from a patient, (b) opening of the patient's chest cavity to expose the patient's heart and (c) excising of the heart valve of the patient's heart needing replacement, thereby leaving an open annulus within the heart, said first kit being a tissue harvesting and annulus sizing kit comprising a tray containing, for rapid availability, the following components for harvesting the tissue and quickly and accurately measuring said open annulus within the patient's heart;

a tissue sized template formed of a soft and flexible bio-compatible material for positioning directly upon the tissue to be harvested with said template being used as a guide to cut a piece of the patient's tissue in the desired configuration;

a series of obturators of different size which the surgeon can selectively push into said open annulus to ascertain the size of the prosthetic heart valve to be constructed during the open heart procedure;

said second kit being a size specific kit as determined by the annulus measured by using said first kit, said second kit comprising a tray containing, for rapid availability, the following components;

a cutting die for cutting out a portion of said harvested tissue along a perimeter sized to said measured annulus, said cutting die having a substantially continuous blade with a plurality of repeating curved segments, an inner and outer stent sized to said measured annulus, and an assembly mandrel for mounting said tissue between said inner and outer stents for permanently assembling a prosthetic heart valve sized to said measured annulus.

3. A pair of first and second pre-fabricated, sterile kits for use during open heart surgery to provide tools and apparatus for very rapidly manufacturing a prosthetic heart valve immediately following (a) harvesting of tissue from a patient, (b) opening of the patient's chest cavity to expose the patient's heart, and (c) excising of a heart valve of the patient's heart needing replacement, thereby leaving an open annulus within the heart, said first kit being a tissue harvesting and annulus sizing kit comprising a tray containing, for rapid availability, the following components for harvesting the tissue and quickly and accurately measuring said open annulus within the patient's heart:

a series of obturators of different size which the surgeon can selectively push into said open annulus to ascertain the size of the prosthetic heart valve to be constructed during the open heart procedure;

said second kit being a size specific kit as determined by the annulus measured by using said first kit, said second kit comprising a tray containing, for rapid availability, the following components:

a cutting die for cutting out a portion of said harvested tissue along a perimeter sized to said measured annulus, said cutting die having a substantially continuous blade with a plurality of repeating curved segments, an inner and outer stent sized to said measured annulus, and an assembly mandrel for mounting said tissue between said inner and outer stents for permanently assembling a prosthetic heart valve sized to said measured annulus.

4. A pre-fabricated, sterile kit for use during open heart surgery to provide tools and apparatus for very rapidly manufacturing a prosthetic heart valve immediately following (a) harvesting of tissue from a patient, (b) opening of the patient's chest cavity to expose the patient's heart, and (c) excising of a heart valve of the patient's heart needing replacement, thereby leaving an open annulus within the heart, said kit comprising a tray containing, for rapid availability, the following components:

a cutting die for cutting out a portion of said harvested tissue along a perimeter sized to said open annulus, said cutting die having a substantially continuous blade with a plurality of repeating curved segments;

an inner and outer stent sized to said open annulus; and an assembly mandrel for mounting said tissue between said inner and outer stents for permanently assembling a prosthetic heart valve sized to said open annulus.

* * * * *